(12) United States Patent
Miller et al.

(10) Patent No.: US 12,162,778 B2
(45) Date of Patent: Dec. 10, 2024

(54) CHEMICAL MONITORING DEVICES AND METHODS

(71) Applicant: Hayward Industries, Inc., Charlotte, NC (US)

(72) Inventors: Justin Miller, Monte Sereno, CA (US); Mark Janes, Los Gatos, CA (US); Josh Kennedy, Sunnyvale, CA (US); Scott Eklund, Cupertino, CA (US)

(73) Assignee: Hayward Industries, Inc., Charlotte, NC (US)

( * ) Notice: Subject to any disclaimer, the term of this patent is extended or adjusted under 35 U.S.C. 154(b) by 43 days.

(21) Appl. No.: 17/409,452

(22) Filed: Aug. 23, 2021

(65) Prior Publication Data

US 2021/0380435 A1   Dec. 9, 2021

Related U.S. Application Data

(63) Continuation of application No. 16/990,730, filed on Aug. 11, 2020, now Pat. No. 11,097,958, which is a
(Continued)

(51) Int. Cl.
*C02F 1/00* (2023.01)
*C02F 1/66* (2023.01)
(Continued)

(52) U.S. Cl.
CPC ............... *C02F 1/008* (2013.01); *C02F 1/66* (2013.01); *C02F 1/685* (2013.01); *C02F 1/76* (2013.01);
(Continued)

(58) Field of Classification Search
None
See application file for complete search history.

(56) References Cited

U.S. PATENT DOCUMENTS

D138,325 S     7/1944  Pool
3,162,470 A   12/1964  Davidson et al.
(Continued)

FOREIGN PATENT DOCUMENTS

CN   103245766 A    8/2013
CN   104251730 A   12/2014
(Continued)

OTHER PUBLICATIONS

D. W. Egles, "RANGER 1: A Self-Propelled Data Buoy," OCEANS '85—Ocean Engineering and the Environment, IEEE Conference Record, Nov. 1985, vol. 1, pp. 56-61.
(Continued)

*Primary Examiner* — Richard C Gurtowski
(74) *Attorney, Agent, or Firm* — McCarter & English, LLP

(57) ABSTRACT

Implementations of this disclosure are directed to systems, devices and methods for monitoring parameters associated with a body of liquid. In one embodiment, a device includes a container configured to be partially submerged in a liquid and includes sensors disposed within a submerged portion of the container to measure parameters associated with the liquid. An electronic component disposed within an unsubmerged portion of the container transmits information related to the parameters based upon which one or more actions related to treatment of the body of liquid are suggested.

39 Claims, 21 Drawing Sheets

Related U.S. Application Data continuation of application No. 15/797,356, filed on Oct. 30, 2017, now Pat. No. 10,737,951, which is a continuation of application No. 15/460,987, filed on Mar. 16, 2017, now Pat. No. 9,834,451.

(60) Provisional application No. 62/310,026, filed on Mar. 18, 2016.

(51) Int. Cl.
  *C02F 1/68* (2023.01)
  *C02F 1/76* (2023.01)
  *H04W 4/38* (2018.01)
  C02F 103/42 (2006.01)
  H04L 67/125 (2022.01)

(52) U.S. Cl.
  CPC ............... *C02F 1/766* (2013.01); *H04W 4/38* (2018.02); C02F 2103/42 (2013.01); C02F 2209/006 (2013.01); C02F 2209/008 (2013.01); C02F 2209/02 (2013.01); C02F 2209/06 (2013.01); C02F 2209/29 (2013.01); H04L 67/125 (2013.01)

(56) References Cited

U.S. PATENT DOCUMENTS

| | | | |
|---|---|---|---|
| 3,803,573 | A | 4/1974 | Schonger |
| D242,618 | S | 12/1976 | Milo |
| D254,266 | S | 2/1980 | Tableriou |
| 4,435,095 | A | 3/1984 | Jones et al. |
| 4,510,487 | A | 4/1985 | Wolfe et al. |
| 4,781,810 | A | 11/1988 | Tucker |
| 4,900,432 | A | 2/1990 | Arnold et al. |
| 4,940,946 | A | 7/1990 | Nazaryan |
| 5,055,183 | A | 10/1991 | Buchan |
| D326,309 | S | 5/1992 | Kendrick |
| 5,115,222 | A | 5/1992 | Peralta et al. |
| 5,124,960 | A | 6/1992 | Miller et al. |
| 5,152,610 | A | 10/1992 | Hallett |
| 5,169,236 | A | 12/1992 | Iest |
| 5,189,350 | A | 2/1993 | Mallett |
| 5,422,014 | A | 6/1995 | Allen et al. |
| 5,518,635 | A | 5/1996 | Kohlman |
| D371,824 | S | 7/1996 | Price et al. |
| 5,681,110 | A | 10/1997 | Burzacchi |
| 5,788,826 | A | 8/1998 | Nyberg |
| 5,915,622 | A | 6/1999 | Foote |
| 5,925,572 | A | 7/1999 | Byrne et al. |
| 5,996,138 | A | 12/1999 | Kentch |
| D422,676 | S | 4/2000 | Conover et al. |
| 6,113,858 | A | 9/2000 | Tang et al. |
| D432,206 | S | 10/2000 | Stoltz et al. |
| D439,313 | S | 3/2001 | Wey et al. |
| 6,223,359 | B1 | 5/2001 | Oltmanns et al. |
| 6,225,900 | B1 | 5/2001 | Keon et al. |
| 6,228,272 | B1 | 5/2001 | Gola |
| 6,238,553 | B1 | 5/2001 | Lin |
| 6,294,086 | B1 | 9/2001 | Reeves |
| 6,309,538 | B1 | 10/2001 | Khan |
| 6,340,431 | B2 | 1/2002 | Khan |
| 6,456,197 | B1 | 9/2002 | Lauritsen et al. |
| 6,476,721 | B1 | 11/2002 | Diebold |
| 6,488,841 | B2 | 12/2002 | Glasgow |
| 6,579,446 | B1 | 6/2003 | Teran et al. |
| D479,475 | S | 9/2003 | Dermikaelien-Covault et al. |
| 6,625,824 | B1 | 9/2003 | Lutz et al. |
| 6,653,842 | B2 | 11/2003 | Mosley et al. |
| 6,697,706 | B2 | 2/2004 | Gardner, Jr. |
| 6,713,298 | B2 | 3/2004 | McDevitt et al. |
| D489,431 | S | 5/2004 | Antunez |
| 6,792,956 | B2 | 9/2004 | Bredo et al. |
| 6,958,693 | B2 | 10/2005 | Rothgeb et al. |
| 7,037,038 | B1 | 5/2006 | Haski et al. |
| D526,382 | S | 8/2006 | Thompson |
| D537,913 | S | 3/2007 | Biberger et al. |
| 7,292,898 | B2 | 11/2007 | Clark et al. |
| D559,943 | S | 1/2008 | Mercer |
| 7,409,853 | B2 | 8/2008 | Biberger et al. |
| 7,681,436 | B2 | 3/2010 | Biberger |
| 7,752,893 | B2 | 7/2010 | Biberger |
| 8,043,070 | B2 | 10/2011 | Stiles, Jr. et al. |
| 8,459,100 | B2 | 6/2013 | Biberger |
| 8,883,079 | B2 | 11/2014 | Clark |
| 8,963,736 | B2 | 2/2015 | Millar |
| 9,031,702 | B2 | 5/2015 | Pruchniewski et al. |
| 9,034,193 | B2 | 5/2015 | Shalon |
| 9,097,234 | B2 | 8/2015 | Breau et al. |
| 9,581,478 | B1 | 2/2017 | Smith |
| 9,631,388 | B2 | 4/2017 | Hui et al. |
| D789,221 | S | 6/2017 | Miller et al. |
| 9,815,719 | B2 | 11/2017 | Sayre et al. |
| 9,834,451 | B2 | 12/2017 | Miller et al. |
| 9,858,792 | B2 | 1/2018 | Fernandes et al. |
| 10,037,675 | B2 | 7/2018 | Uy |
| 10,102,585 | B1 | 10/2018 | Bryant et al. |
| 10,127,362 | B2 | 11/2018 | Bennett et al. |
| 10,255,784 | B2 | 4/2019 | Uy |
| 10,306,340 | B2 | 5/2019 | Goldberg et al. |
| 10,375,543 | B2 | 8/2019 | McQueen et al. |
| 10,378,544 | B2 | 8/2019 | Rejniak et al. |
| 10,560,820 | B2 | 2/2020 | McQueen et al. |
| 10,618,136 | B2 | 4/2020 | Bauckman et al. |
| 10,737,951 | B2 | 8/2020 | Miller et al. |
| 10,989,200 | B2 | 4/2021 | Rejniak et al. |
| 11,100,465 | B1 | 8/2021 | Le Burge |
| 2001/0045380 | A1 | 11/2001 | Khan |
| 2002/0035403 | A1 | 3/2002 | Clark et al. |
| 2002/0195403 | A1 | 12/2002 | Takeda et al. |
| 2003/0227394 | A1 | 12/2003 | Rothgeb et al. |
| 2004/0031329 | A1 | 2/2004 | Carpenter et al. |
| 2004/0066313 | A1 | 4/2004 | Ong et al. |
| 2004/0197229 | A1 | 10/2004 | Runyon |
| 2004/0208499 | A1 | 10/2004 | Grober |
| 2005/0139530 | A1* | 6/2005 | Heiss ..................... C02F 9/00 210/257.2 |
| 2005/0207939 | A1 | 9/2005 | Roussi et al. |
| 2005/0220169 | A1 | 10/2005 | Mcgowan-Scanlon |
| 2005/0225766 | A1 | 10/2005 | Hansen et al. |
| 2005/0279677 | A1 | 12/2005 | Lin |
| 2006/0096927 | A1 | 5/2006 | Clukies |
| 2007/0013381 | A1 | 1/2007 | Biberger |
| 2008/0311898 | A1 | 12/2008 | Benco et al. |
| 2009/0210081 | A1 | 8/2009 | Sustaeta et al. |
| 2010/0270228 | A1* | 10/2010 | Teichberg ...... C12Y 305/02015 435/231 |
| 2011/0009019 | A1 | 1/2011 | Neira et al. |
| 2011/0121036 | A1 | 5/2011 | Bassett |
| 2011/0214500 | A1 | 9/2011 | Cabrera et al. |
| 2012/0078426 | A1 | 3/2012 | Macey |
| 2012/0185571 | A1 | 7/2012 | Uy |
| 2013/0098849 | A1 | 4/2013 | Doyle et al. |
| 2013/0104321 | A1 | 5/2013 | Michelon |
| 2013/0313204 | A1 | 11/2013 | Shalon |
| 2014/0064139 | A1 | 3/2014 | Mcqueen et al. |
| 2014/0124454 | A1 | 5/2014 | Nichols et al. |
| 2014/0200840 | A1 | 7/2014 | Cox et al. |
| 2014/0266755 | A1 | 9/2014 | Arensmeier et al. |
| 2015/0092055 | A1 | 4/2015 | Scalisi et al. |
| 2015/0310634 | A1 | 10/2015 | Babcock et al. |
| 2016/0042629 | A1 | 2/2016 | Snyder |
| 2016/0061640 | A1 | 3/2016 | Joshi et al. |
| 2016/0259348 | A1 | 9/2016 | Lewis et al. |
| 2016/0266577 | A1 | 9/2016 | Kerzner |
| 2017/0092096 | A1 | 3/2017 | Fernandes et al. |
| 2017/0170979 | A1 | 6/2017 | Khalid et al. |
| 2017/0203980 | A1 | 7/2017 | Buzaglo et al. |
| 2017/0206615 | A1 | 7/2017 | Sloop et al. |
| 2017/0209338 | A1 | 7/2017 | Potucek et al. |
| 2017/0212530 | A1 | 7/2017 | Potucek et al. |
| 2017/0249285 | A1 | 8/2017 | Stewart et al. |
| 2017/0336381 | A1 | 11/2017 | Zeevi |
| 2017/0346688 | A1 | 11/2017 | Reddy et al. |

(56) References Cited

U.S. PATENT DOCUMENTS

| | | | |
|---|---|---|---|
| 2018/0130328 A1 | 5/2018 | Fernandes et al. |
| 2018/0224822 A1 | 8/2018 | Potucek et al. |
| 2018/0373304 A1 | 12/2018 | Davis et al. |
| 2019/0087548 A1 | 3/2019 | Bennett et al. |
| 2019/0180595 A1 | 6/2019 | Uy |
| 2020/0369535 A1 | 11/2020 | Miller et al. |
| 2021/0026727 A1 | 1/2021 | Minehan et al. |

FOREIGN PATENT DOCUMENTS

| | | | |
|---|---|---|---|
| CN | 204165969 U | 2/2015 |
| CN | 204495401 U | 7/2015 |
| DE | 19951436 A1 | 5/2000 |
| DE | 19921436 A1 | 11/2000 |
| EP | 0821514 A1 | 1/1998 |
| EP | 1600749 A1 | 11/2005 |
| EP | 1913216 A2 | 4/2008 |
| GB | 2365122 A | 2/2002 |
| WO | 03/012434 A2 | 2/2003 |
| WO | 03/087501 A1 | 10/2003 |
| WO | 03/091668 A2 | 11/2003 |
| WO | 2004/019295 A1 | 3/2004 |
| WO | 2005/008443 A2 | 1/2005 |

OTHER PUBLICATIONS

William R. Griffen, "Maintaining Swimming Pools, Spas, Whirlpool Tubs, and Saunas" (2001), retrieved from the Internet at <http://www.cleaningconsultants.com/pages/articles/poolsspas.html> (8 pages).

"Water Chemistry for Swimming Pools", North Carolina Department of Environment and Natural Resources, Feb. 2001, retreived from the internet archive at <https://web.archive.org/web/20010207022454/http://www.deh.enr.state.hc.us/ehs/quality/wph.htm> (12 pages).

Office Action mailed May 19, 2017, issued in connection with U.S. Appl. No. 15/460,987 (11 pages).

Interview Summary mailed Jun. 7, 2017, issued in connection with U.S. Appl. No. 15/460,987 (3 pages).

PCT International Search Report and Written Opinion of the International Searching Authority mailed Jul. 19, 2017, Issued in connection with International Application No. PCT/US2017/022656 (10 pages).

Notice of Allowance mailed Aug. 18, 2017, issued in connection with U.S. Appl. No. 15/460,987 (9 pages).

Notice of Allowance mailed Oct. 27, 2017, issued in connection with U.S. Appl. No. 15/460,987 (8 pages).

Office Action mailed Apr. 8, 2019, issued in connection with U.S. Appl. No. 15/797,356 (13 pages).

Partial Supplementary European Search Report dated Nov. 7, 2019, issued in connection with European Patent Application No. 17767502.2 (10 pages).

Office Action mailed Nov. 27, 2019, issued in connection with U.S. Appl. No. 15/797,356 (8 pages).

Advisory Action mailed Feb. 5, 2020, issued in connection with U.S. Appl. No. 15/797,356 (3 pages).

Extended European Search Report dated Feb. 10, 2020, issued in connection with European Patent Application No. 17767502.2 (9 pages).

Notice of Allowance mailed Apr. 1, 2020, issued in connection with U.S. Appl. No. 15/797,356 (11 pages).

Examination Report dated Sep. 18, 2020, issued in connection with European Patent Application No. 17767502.2 (3 pages).

Office Action mailed Dec. 18, 2020, issued in connection with U.S. Appl. No. 16/990,730 (8 pages).

PCT Invitation to Pay Additional Fees mailed Dec. 29, 2020, in connection with International Application No. PCT/US2020/058058 (3 pages).

PCT International Search Report and Written Opinion of the International Searching Authority mailed Mar. 2, 2021, in connection with International Application No. PCT/US2020/058058 (13 pages).

Notice of Allowance mailed Apr. 14, 2021, issued in connection with U.S. Appl. No. 16/990,730 (10 pages).

Examination Report dated May 20, 2021, issued in connection with Australian Patent Application No. 2017232651 (2 pages).

Restriction Requirement dated Dec. 29, 2022, issued in connection with U.S. Appl. No. 17/774,314 (7 pages).

* cited by examiner

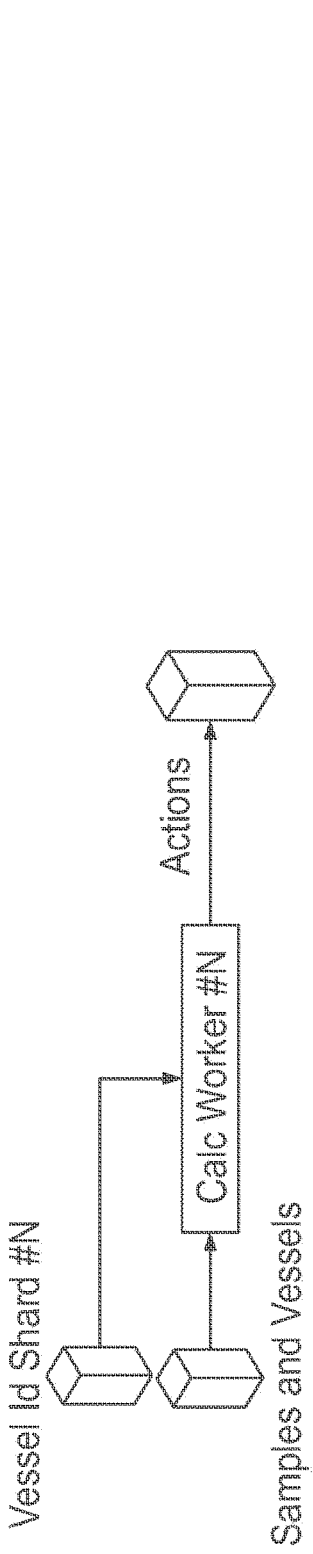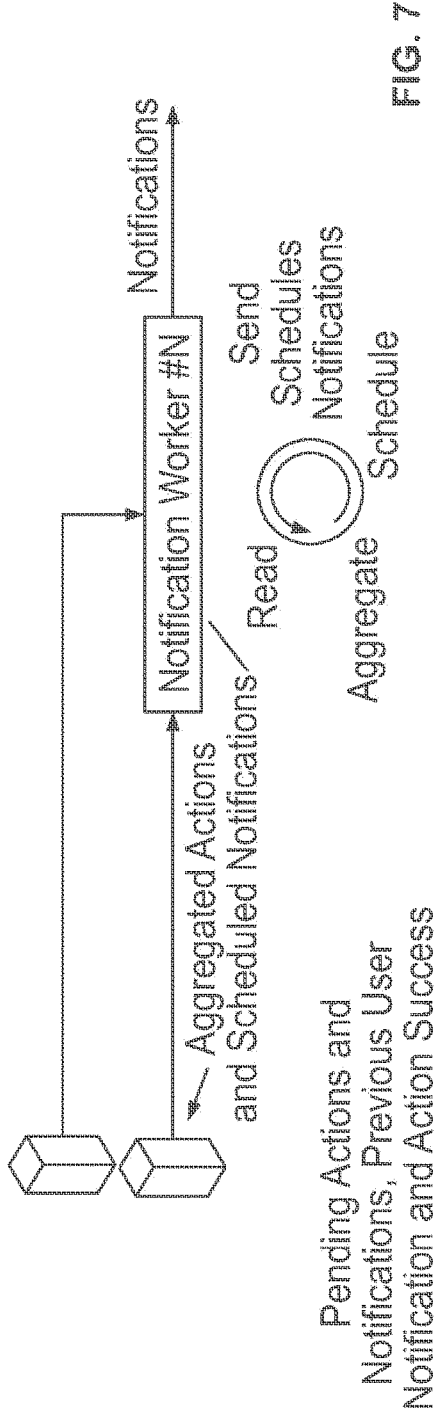
FIG. 7

$V_i := \text{vessel}, P_i := \text{protocol}, I_i := \text{inventory}$ $p_i := \text{product}, S_i := \text{sensor history}$ $\vec{\Pi}_i := \text{product additions \& effect of each}$ $q_i := \text{quantity}, \Pi_i^t := \text{past confirmed actions}$ $P \rightarrow \text{Chemical classes, danger bands}$ $V \rightarrow P, I, S, \text{volume, action history, location}$ $I \rightarrow \{(p, q), \ldots\}$ $V \rightarrow S$ $S \otimes (P, V, \Pi^t) \rightarrow \{\delta_{\text{sanitizer}}, \delta_{\text{ph}}, \ldots\} = \vec{\delta} \;(\text{chemical demand vector to hit ideal})$ $\vec{\delta} \otimes (P, I, V) \rightarrow \{(p_{\text{sanitizer}}, q_{\text{sanitizer}} \times \vec{\delta}_{\text{sanitizer}} \times \vec{\delta}_{\text{sanitizer}}), (p_{\text{ph}}, q_{\text{ph}} \times \vec{\delta}_{\text{ph}}), \ldots\} = \vec{\Pi} \;(\text{product additions \& effect of each})$

FIG. 8

CHEMICAL MONITORING DEVICES AND METHODS

RELATED APPLICATIONS

This application is a continuation of, and claims the benefit of priority to, U.S. patent application Ser. No. 16/990,730 filed on Aug. 11, 2020 (issued as U.S. Pat. No. 11,097,958), which is a continuation of, and claims the benefit of priority to, U.S. patent application Ser. No. 15/797,356 filed on Oct. 30, 2017 (issued as U.S. Pat. No. 10,737,951), which is a continuation of, and claims the benefit of priority to, U.S. patent application Ser. No. 15/460,987 filed on Mar. 16, 2017 (issued as U.S. Pat. No. 9,834,451), which claims the benefit of priority to U.S. Provisional Application Ser. No. 62/310,026, filed on Mar. 18, 2016 and entitled "Connected Pool Monitoring System," the entire disclosures of which are expressly incorporated by reference herein.

FIELD OF THE INVENTION

In general, embodiments of this disclosure relate to monitoring and adjusting chemical levels in a liquid and, in particular, to systems and methods for monitoring and adjusting chemical levels in a swimming pool or a hot tub.

BACKGROUND

Measuring and maintaining the quality of water is important in a wide variety of circumstances. For example, water in swimming and diving pools, hot tubs, and other sports, recreational, and therapeutic bodies of water need to be kept at certain levels of quality not only to maintain that water's clarity, but also to keep the users of these bodies of water safe from waterborne illnesses. Many homeowners try to manage the chemical levels and water quality themselves using litmus paper, reagent drops and other over the counter testing kits, while others rely on third party services. Each of these approaches has its benefits, but also many drawbacks. What is needed is a device and service that provides reliable, accurate monitoring and chemical delivery services to the homeowner without having to rely exclusively on an on-site professional.

SUMMARY OF THE INVENTION

The invention provides a device and supporting systems and methods for automating and streamlining the management and monitoring of bodies of water, and, specifically, pools and spas. In one aspect, an easy-to-use, internet-connected device that can be literally "thrown into a pool" continuously measures numerous characteristics of the pool (e.g., chemical components, water level, stray voltage, etc.) and, via a wireless antenna, transmit the measurements to a local client application and/or a multi-tenant hosted service for analysis. The analysis may be used, for example, to suggest immediate actions to be taken to address deficiencies, safety concerns, or other conditions of the pool identified by the device. In addition, characteristics of the pool (either user provided or calculated) can be used to assign "treatment protocols" to a pool, which can predict actions and identify measurement outliers that may be safely ignored.

Data from the system may be used to suggest or sell supplies (e.g., color-coded chemical pods) which are packaged in a manner that makes selection and application easy for the homeowner. In some cases, data collected from a pool may be shared with others, such as pool service technicians, neighbors, or others to allow for delegation of tasks to third parties.

Therefore, in a first aspect, the invention provides a device for monitoring and measuring characteristics of a liquid within a bounded body of water such as a swimming pool or spa, or other body of water. The device includes a container configured to be partially submerged in a liquid that encases a sensor for measuring parameters associated with the liquid disposed within a submerged portion of the container and an electronic component disposed within an unsubmerged portion of the container that wirelessly transmits information related to the parameters. The device also includes a switch disposed within the unsubmerged portion of the container for initiating power to the electronic component by application of a magnetic field applied externally to the container and adjacent to the switch.

In some embodiments, the container is void of externally accessible controls, thereby rendering the device waterproof. The sensor may include any one or combination of a pH sensor, a chlorine sensor, a bromine sensor, a temperature sensor, and a voltage meter, which may measure and report parameters such as pH, chlorine level, bromine level, temperature, and stray voltage. The submerged portion may include one or more defined openings that permit the liquid to contact the sensor and capture parameter measurements. The electronic components of the device may include a processor, memory, wireless transceiver, sensor interface, accelerometer, and battery.

In some versions, the accelerometer measures an orientation of the device, such that while the device is oriented such that the submerged portion of the container is no longer substantially below the unsubmerged portion, transmission of the information is paused. In other versions, measurements taken while the accelerometer indicates that the device is not properly submerged may be transmitted to an application or service, but identified as suspect measurements.

In another aspect, the invention provides a system for monitoring a liquid. The system includes a monitoring device comprising a container configured to be partially submerged in a body of water, a sensor disposed within the submerged portion of the container for measuring parameters associated with the water, and an electronic component disposed within an unsubmerged portion of the container for wirelessly transmitting information related to the at least one parameter, and a monitoring application for (i) receiving the information related to the at least one parameter, identifying actions to be taken in response to the information and transmitting instructions to initiate the actions to a client application associated with the body of water.

In some embodiments, the monitoring device may include a switch disposed within the unsubmerged portion of the container for initiating power to the electronic component by application of a magnetic field applied externally to the container and adjacent to the switch. The sensor may include one or more of a pH sensor, a chlorine sensor, a bromine sensor, a temperature sensor, and a voltage meter, which may be used to detect or measure any combination of pH, chlorine level, bromine level, temperature, and stray voltage.

Some versions of the device may include one or more openings in the submerged portion of the device that permit the liquid to contact the sensor, and thus collect the measurements. The electronic component may include a processor, memory, wireless transceiver, sensor interface, accelerometer, and battery. In some embodiments, the accelerometer may be used to measure and provide an orientation of the device, such that while the device is oriented such that the submerged portion of the container is no longer substantially below the unsubmerged portion, transmission of the information is paused and/or tagged as potentially inaccurate.

In another aspect, the invention provides a method for managing chemical levels within an artificial recreational body of water. The method includes providing a monitoring device, a monitoring application, and color-coded additive pods. The device includes a container configured to be partially submerged in the body of water, a sensor disposed within a submerged portion of the container for measuring parameters associated with the body of water, and an electronic component disposed within an unsubmerged portion of the container for wirelessly transmitting information related to parameters. The monitoring application receives the information related to the parameters, identifies actions to be taken in response to the information using a color-coded message, and transmits instructions to initiate the actions to a client application associated with the body of water. The additive pods are color-coded to match the associated message, and when added to the body of water, accomplish the identified one or more actions.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 7 is an example of a message notification process in accordance with one embodiment of the invention.

FIG. 8 is an exemplary algorithm for determining actions to be taken in response to measurement data according to one embodiment of the invention.

DETAILED DESCRIPTION

This disclosure describes a connected pool monitoring system. The system includes a monitoring device for monitoring chemical parameters and temperature of a swimming pool. The system notifies a user (e.g., a customer) about the pool's current condition and any actions that need the user's attention. The system can also fulfill and schedule supplies and services for users and owners of swimming pools, hot tubs, and other bodies of water or other liquid that may need to be monitored and/or treated. Such bodies of liquid are referred to generally herein as "swimming pools" or "pools," although use of that terminology is intended to cover other bodies of liquid not normally referred to as swimming pools or pools, including spas and hot tubs.

In this disclosure, like reference numbers and designations in the various drawings indicate like elements.

Figure 1:
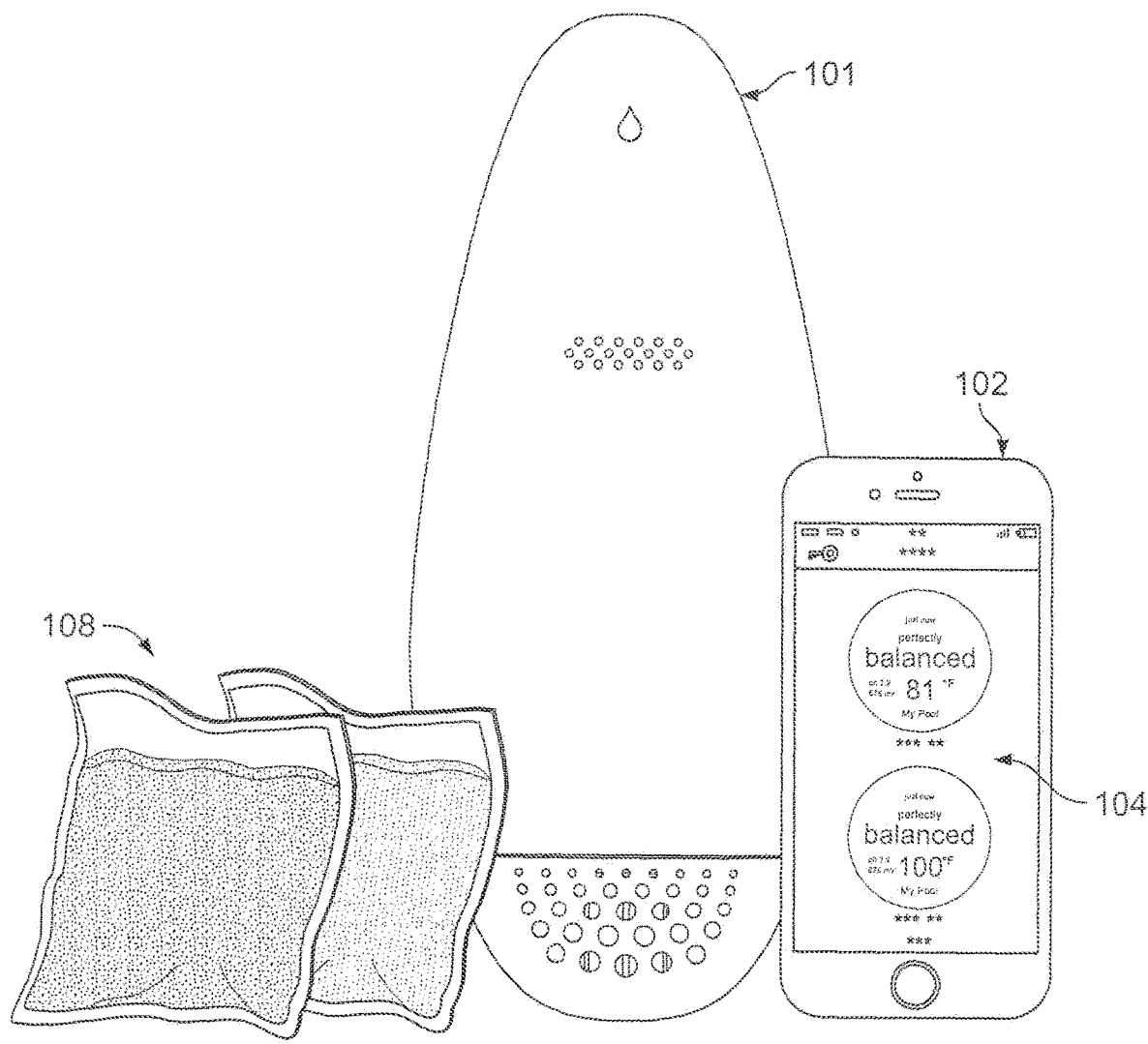
FIG. 1 illustrates an example device and associated client application user interface and chemical pods in accordance with one embodiment of the invention.

FIG. 1 illustrates an example monitoring device 101 (also referred to as a "pHin"). The monitoring device 101 can monitor a swimming pool's parameters, such as pH value, chlorine level, bromine level, oxygen reduction potential (i.e., ORP, which in general is a measure of how much chlorine or bromine is in the pool water), water temperature, total hardness, total alkalinity, cyanuric acid level, total dissolved solids, phosphate levels, and/or metal levels. Other chemical and environmental parameters monitored by the monitoring device 101 are possible. In some implementations, the device 101 includes or utilizes test strips that may be scanned with a camera or other optical device to determine one or more of the pool water parameters. Such scanning may be performed using a mobile device or a camera or scanner integrated into the monitoring device 101.

In some embodiments, the device 101 may float about the pool untethered and unanchored. This permits the device 101 to collect parameters at various positions within the pool, e.g., shallow and deep ends, near or far from water sources, in direct sunlight or shadows, etc. In such cases, a user can "toss" the device 101 into the pool without having to attach it to any anchoring devices or fixtures. In other instances, the device 101 may be restrained into or restricted away from particular areas of the pool by a tethering line.

The monitoring device 101 is configured to connect wirelessly to a client device 102 of a user (e.g., an owner of the swimming pool). In preferred examples, the monitoring device 101 is also configured to connect wirelessly to a Hub (e.g., a BLE-Wifi Bridge) that allows the monitoring device 101 to be connected to the Internet, even when the user and/or the user's client device are not nearby. The wireless connection between the monitoring device 101 and the client device 102 or the Hub can be based on Bluetooth protocol, for example. Other protocols for the wireless connection between the monitoring device 101 and the client device 102 or the Hub are possible. An application running on the client device 102 can present a user interface 104 that is configured to display parameters of the swimming pool transmitted from the monitoring device 101. The user interface 104 can also display notifications such as supply level or user actions. For instance, a notification can be a user action for the user to add a particular chemical for maintaining a desired sanitary or chemical level in or for the swimming pool.

In some instances the application running on the client device 101 may access photos stored on the client device. The photos may include, for example, photos images of test strips used to measure one or more chemical attributes of the pool water.

After seeing the notification, the user can drop one or more packages or pods 108 containing a particular chemical into the swimming pool. Packaging of a pod 108 can dissolve in water, thereby releasing contents of the pod 108 into the water. In one example, the packaging is made of or includes a polymer that dissolves in water, such as polyvinyl alcohol (PVA). Alternatively or additionally, the user may simply cut open the packaging and pour the contents of the pod 108 into the water. The pods 108 or the contents of the pods can be color-coded to identify the one or more specific chemicals inside the pods 108. For example, the chemical to color mapping may be or include the following: Trichlor tabs—Light Green; pH Down—Yellow; pH UP—Orange; Bromine Tablets—Red; Sodium Bromide—Purple; Dichlor—Dark Blue; Trichlor Stix—Light Blue; Non Chlorine Shock—Dark Green. Alternatively or additionally, the pods 108 may include a label that identifies the one or more chemicals and/or amounts of the one or more chemicals within the pods 108. The label may include, for example, the word "Blue," "Blue Chlorine," or "Blue Dichlor," etc.

Figure 2A:
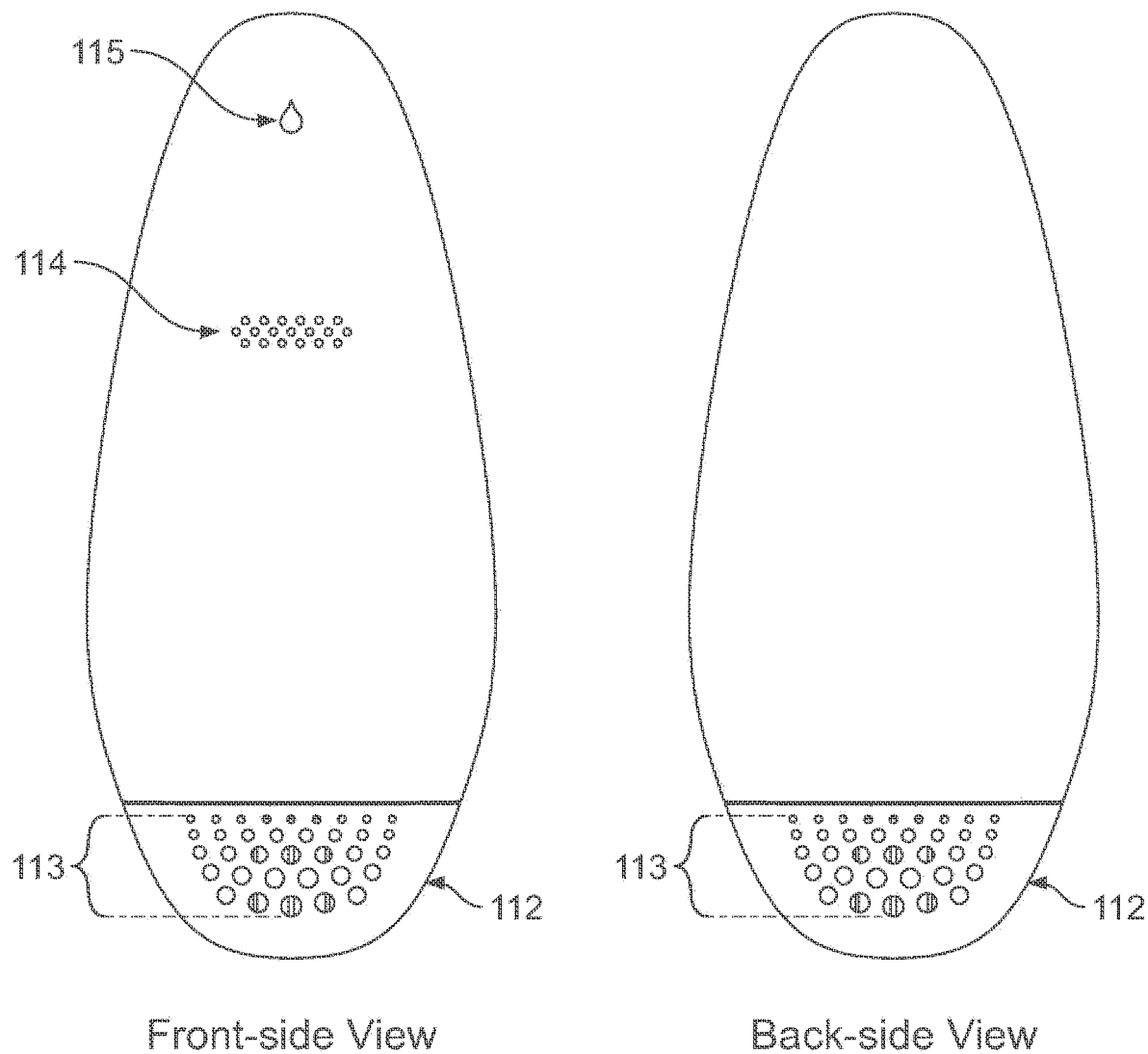
FIG. 2A is a front-side view and back-side view of a device in accordance with one embodiment of the invention.
Figure 2B:
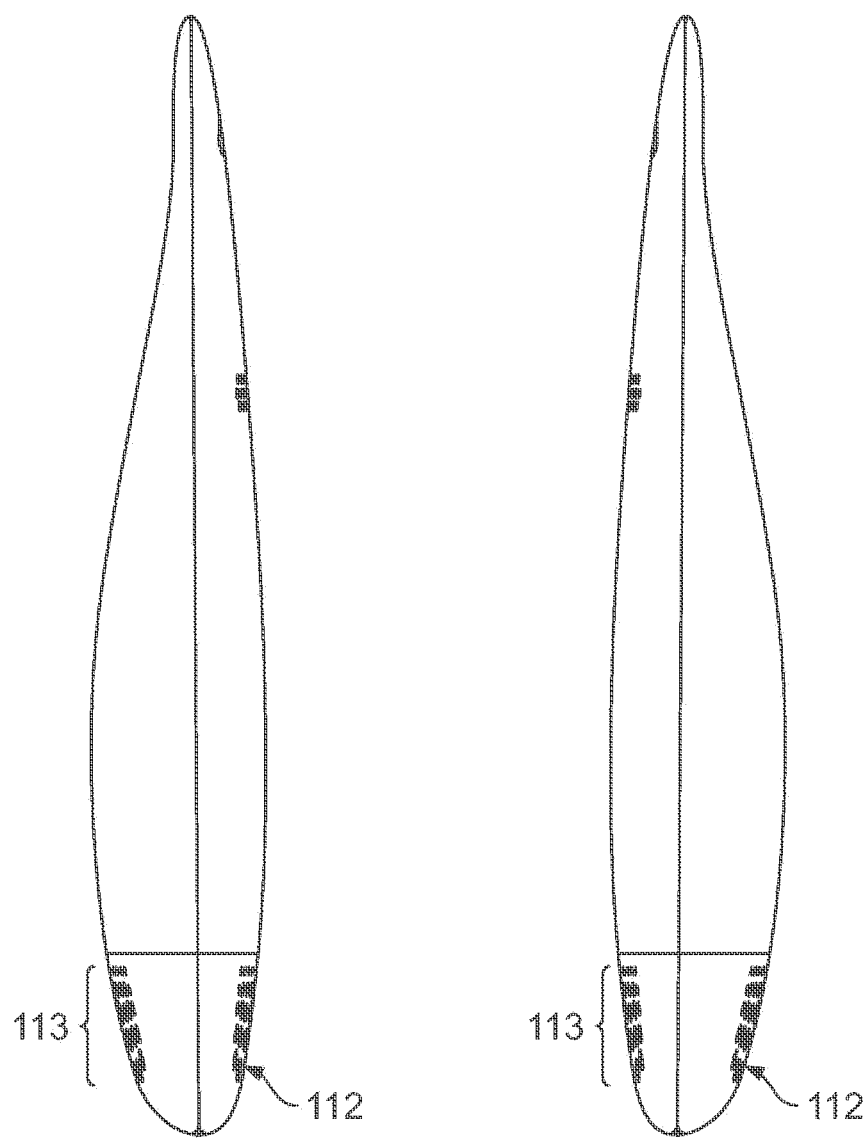
FIG. 2B is a side-view of a device in accordance with one embodiment of the invention.
Figure 2C:
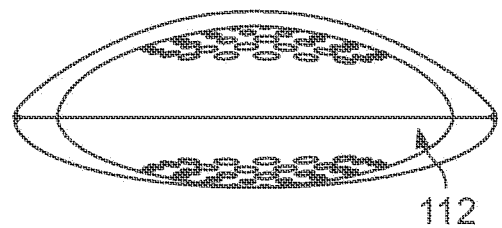
FIG. 2C is a top-view of a device in accordance with one embodiment of the invention.
Figure 3:
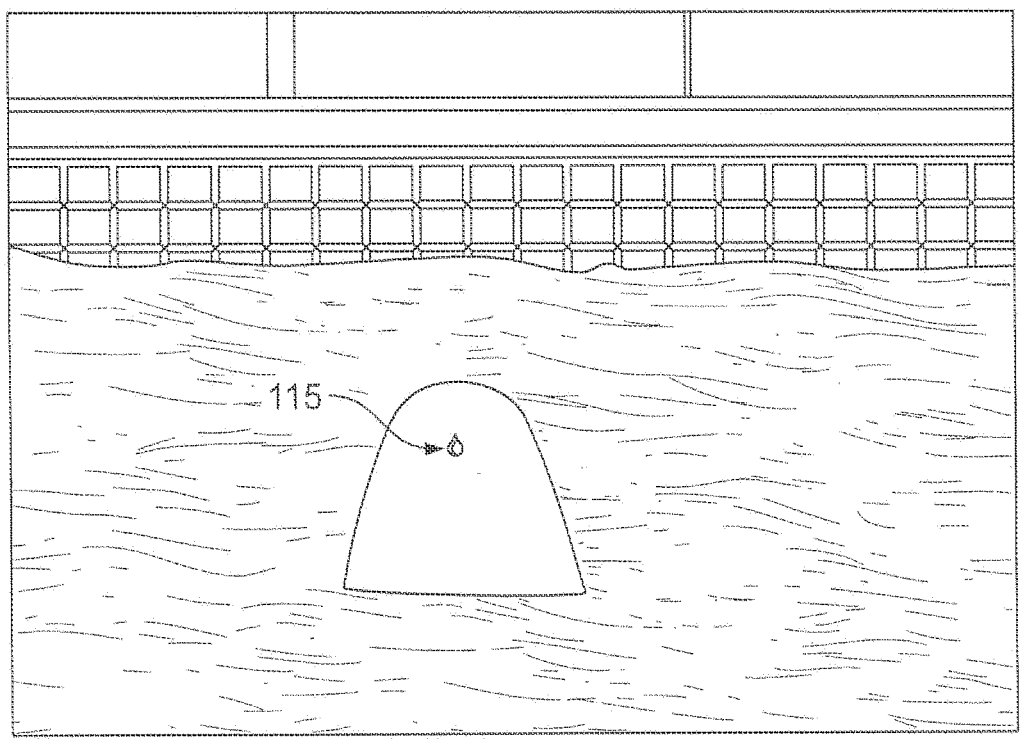
FIG. 3 illustrates a partially-submerged device in accordance with one embodiment of the invention.

FIG. 2A illustrates a front-side view and back-side view of the monitoring device 101. FIG. 2B illustrates side views of the monitoring device 101. FIG. 2C illustrates a view from the bottom-side of the monitoring device 101. The monitoring device 101 includes a bottom cap 112 that can be removed by a user. The bottom cap 112 includes or defines a plurality of openings 113 (e.g., round holes of various sizes) that are configured to allow water to enter the interior of the monitoring device 101. The monitoring device 101 also includes openings such as openings 114 and 115 above the openings 113. The openings 114 and 115 allow air to be pushed out of the interior of the monitoring device 101 when water enters the interior of the monitoring device 101 through the openings 113. In this way, water can function as ballast for the monitoring device 101. The monitoring device 101, like a floating vessel, can float upright and partially submerged in a swimming pool, as illustrated in FIG. 3. As shown in FIG. 3, an unsubmerged top portion including the opening 115 can be above the water of the swimming pool, while the remainder of the monitoring device 101, including sensors of the monitoring device 101, is submerged in the water of the swimming pool, as will be further described later.

In certain embodiments, the device 101 may be sized and weighted to facilitate ease of use by consumers in residential pools and spas. The chart below details ranges and preferred values for certain parameters:

| Parameter | Minimum | Preferred Embodiment | Maximum |
|---|---|---|---|
| Height | 10 cm | 25 cm | 50 cm |
| Width | 5 cm | 11 cm | 20 cm |
| Depth | 2 cm | 4 cm | 8 cm |
| Weight | 30 grams | 300 grams | 1 kg |
| % Submerged | 30% | 75% | 90% |

Figure 4:
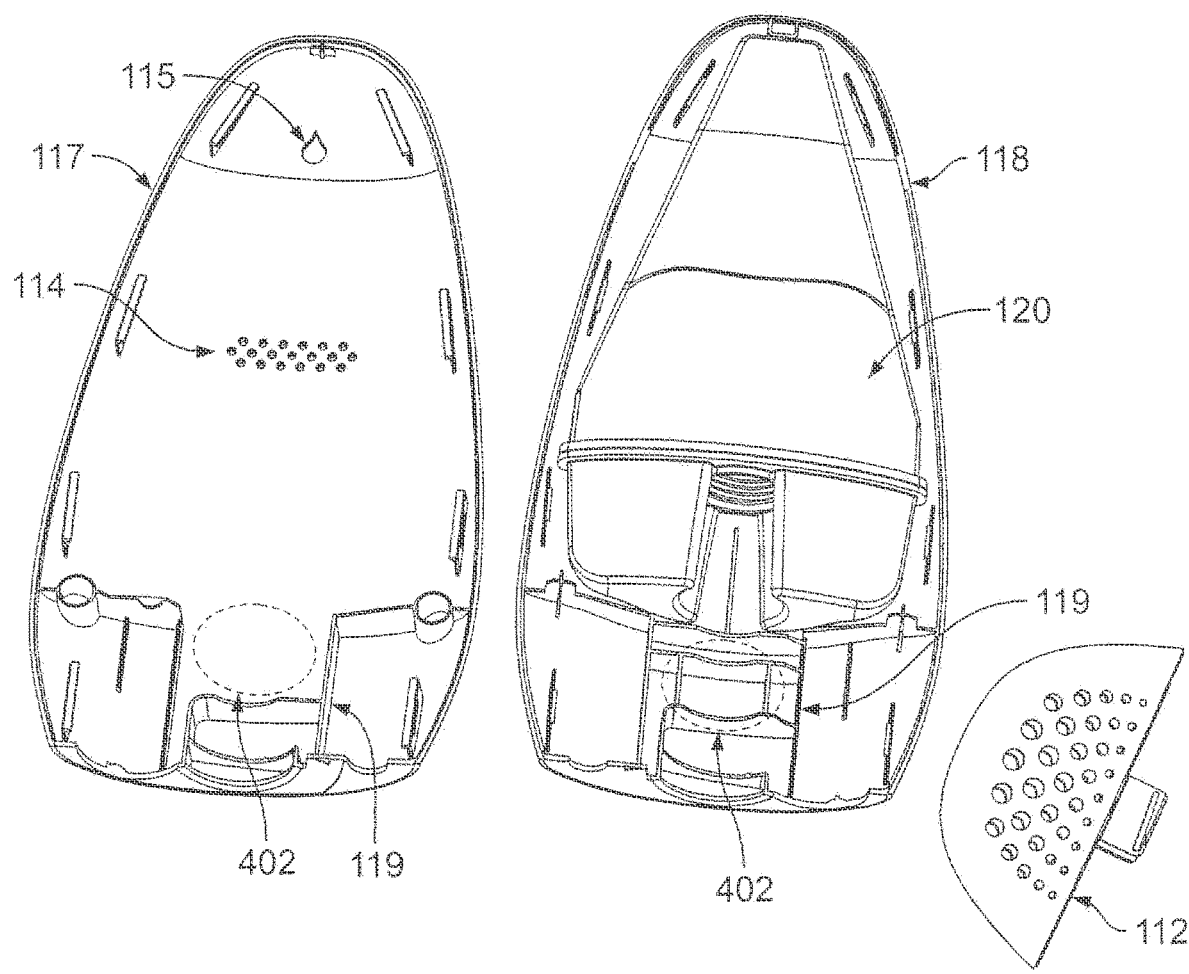
FIG. 4 is an interior view of a device in accordance with one embodiment of the invention.

FIG. 4 illustrates part of the interior of the monitoring device 101. An exterior container or shell of the monitoring device 101 includes the bottom cap 112, a front cover 117, and a back cover 118. The front cover 117 includes the openings 114 and 115 described earlier. The front and back covers 117 and 118 can include flanges 119 that can be used to enhance structural rigidity of the covers. The flanges can also be placed in the lower portion of the covers such that the flanges can function as ballast for the monitoring device 101 floating upright in the water. Lower portions of the covers 117 and 118 can have thicker walls than those of upper portions of the covers 117 and 118 such that the thicker walls at the lower portions can function as ballast for the monitoring device 101 floating upright in water. The covers 117 and 118, and the bottom cap can be made of plastic material (e.g., polypropylene, polyethylene, vinyl, polyester, polycarbonate, XENOY, or combinations thereof) that is resistant to damages from impact, sunlight, and chlorine (or other chemicals in a swimming pool), for example.

In FIG. 4, a bladder 120 (a hollow chamber) holds a board that contains electronics of the monitoring device 101. Sensors of the monitoring device 101 can be placed in a space 402. The sensors are connected to the board in the bladder 120, as described further below. The bladder 120 can be made of plastic material (e.g., acrylonitrile butadiene styrene or ABS) that is resistant to deformation and damages from impact, chemicals, and/or heat, for example.

Figure 5:
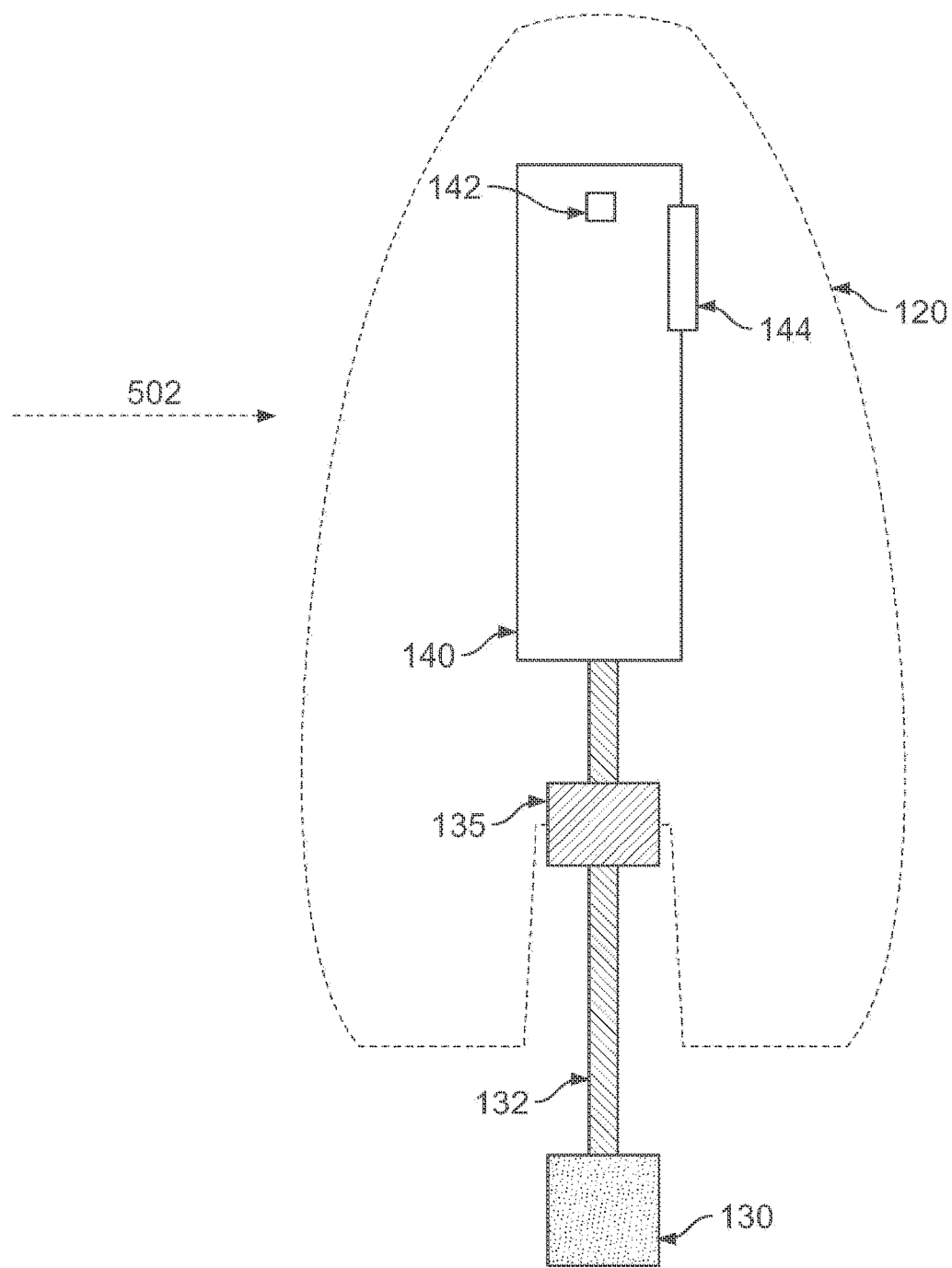
FIG. 5 is an interior view of sensors disposed within a device in accordance with one embodiment of the invention.

FIG. 5 illustrates an example arrangement of sensors 130 and board 140 inside the monitoring device 101. A connection 132 connects the sensors 130 and the board 140. The connection 132 can include wiring between the sensors 130 and components on the board 140. As described earlier, the board 140 is located in the interior of the bladder 120. A water-proof sealing 135 can be used to keep water and moisture from the interior of the bladder 120. The water-proof sealing 135 can include one or more O-rings and threads in contact with the wall of the bladder 120, for example.

The board 140 (e.g., a printed circuit board or PCB) contains electronics or electronic components of the monitoring device 101. The electronic components on the board 140 can include a processor, memory, Bluetooth transceiver, sensor interfaces, and battery, for example. The board 140 also includes a light-emitting diode (LED) indicator 142 and a reed switch 144. Other electronic components are possible. For instance, the board 140 can include an accelerometer that can be used to measure orientation and velocity of the monitoring device 101. The LED indicator can be placed in the vicinity of the opening 115 described earlier, such that lighting of the LED indicator can be seen from outside of the monitoring device 101. As described in reference to FIG. 3, when the monitoring device 101 floats upright in a swimming pool, the top portion (including the opening 115) of the monitoring device 101 can be above water level 502, while the rest (lower portion) of the monitoring device 101 is submerged under the water level 502. In this way, lighting of the LED indicator can be visible from outside of the monitoring device 101 (above water level), while the sensors 130 are submerged in the swimming pool and are configured to monitor chemical and environmental parameters of water in the swimming pool.

The sensors 130 can include a pH sensor, an ORP sensor, a temperature sensor, a chlorine level sensor, a bromine level sensor, a total hardness sensor, a total alkalinity sensor, a cyanuric acid level sensor, a total dissolved solids sensor, a phosphate level sensor, and/or a metal level sensor. Other types of sensors are possible. The sensors 130 can be configured to read chemical and environmental parameters at a specified reading interval (e.g., every 10 milliseconds, every second, every 15 minutes, every hour, or once per day) to conserver the battery. The reading frequency can also be configured to adjust depending time of the day. For instance, readings by the sensor 130 can be more frequent (e.g., every 10 minutes) during the day (e.g., between 9 o'clock in the morning and 6 o'clock in the afternoon) when more pool usage is higher (thus more variations in monitored parameters). Readings by the sensor 130 can be less frequent (e.g., every 60 minutes) during night when less or no pool usage is expected (thus less variations in monitored parameters). Other reading frequency settings are possible. For instance, the reading frequency can become higher (e.g., from every 15 minutes to every 5 minutes) when the monitoring device 101 observes more changes (fluctuations) in parameters measured by the sensors 130.

The reed switch 144 is an electrical switch that can be in a conducting state (ON) or non-conducting state (OFF) depending on the presence of a magnetic field (that is different from the earth's magnetic field). For instance, the reed switch 144 can be non-conducting in the presence of a magnetic field (e.g., from a magnet) and conducting when the magnetic field is removed, or vice versa. The reed switch 144 can function as a user input device in place of push buttons as push buttons can be prone to water damage, for example. In various implementations, the monitoring device 101 can be shipped in a shipping box. The shipping box may, in some instances, include a magnet that is placed near the reed switch 144 when the monitoring device 101 is placed inside the box. In this way, when the monitoring device 101 is inside the box, the magnet can turn off the reed switch 144 and the entire board 140 such that no electricity is drawn from the battery, thus conserving the battery during shipment of the monitoring device 101. When a user removes the monitoring device 101 from the shipping box, the reed switch 144 and the entire board 140 is turned on, and the electronics of the monitoring device 101 is activated. At a later time, the user can place the monitoring device 101 in the shipping box then remove it from the shipping box to reset the electronics of the monitoring device 101, for example. The user can also place the monitoring device 101 in the shipping box and turn off the electronics of the monitoring device 101 when the device is not in use (e.g., during winter).

In other embodiments, the magnet may be provided as a separate element which may be removed from the box after opening, thus allowing the user to discard the box while still using the magnet to activate and deactivate the reed switch 144. As such, the device 101 may be turned on, off and reset without the need for external switches or buttons that may threaten the waterproof nature of the device 101.

Other user input functions provided by the reed switch 144 are possible. For instance, a user can place the monitoring device 101 near a magnet (e.g., placing in the shipping box) for a specified time period (e.g., 10 seconds) then remove the monitoring device 101 away from the magnet to erase content stored in the memory on the board 140.

The accelerometer on the board 140 can be used to detect an orientation of the monitoring device 101. For instance, when the accelerometer detects the monitoring device 101 is being placed horizontally (e.g., placed on its side) and is stationary for an extended period of time (e.g., 30 minutes), that is, not floating vertically in water, the monitoring device 101 can determine that it has been outside of a swimming pool. The monitoring device 101 can send a notification to the client device 102, causing the client device 102 to display in the user interface 104 an alert to the user. In some instances, measurements received while the accelerometer indicates that the device 101 is not in the pool may be ignored, as it is likely that the measurements are not accurate or relevant.

In some embodiments, the device 101 may also include a voltage meter for measuring stray voltage within the water. For example, if wiring of a pump, light, or other source electrical current were in contact with the pool water, stray current may be present, thus creating a hazard to anyone using the pool. In such cases, measurements may trigger a sound or light warning on the device 101 indicating it is not safe to enter the water. In some cases, the alert may be sent to and displayed within an application operating on a user's mobile phone—thus allowing the alert to be delivered to an individual who is not necessarily in the same vicinity of the pool (e.g., a parent at work).

Figure 6:
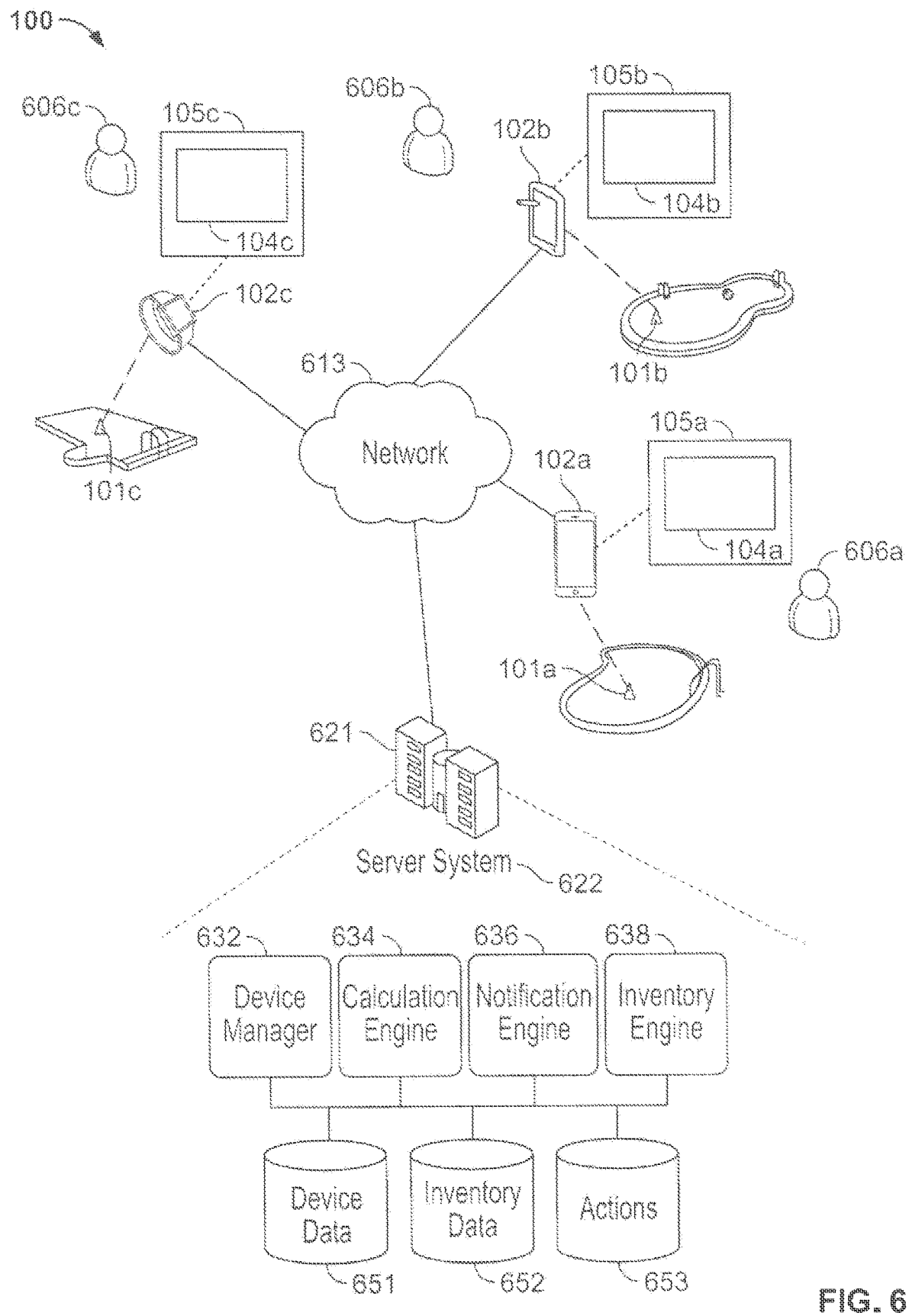
FIG. 6 is an example of a swimming pool monitoring system in accordance with one embodiment of the invention.

FIG. 6 illustrates an example swimming pool monitoring system. In FIG. 6, a server system 622 provides functions for managing pool monitoring devices such as the monitoring device 101 described earlier. The server system 622 comprises software components and databases that can be deployed in one or more datacenters 621 in one or more geographical locations, for example. The server system 622 software components comprise a device manager 632, calculation engine 634, notification engine 636, and inventory engine 638. The server system 622 databases comprise a device data database 651, inventory data database 652, and actions database 653. The databases can reside in one or more physical storage systems. The software components and databases will be further described below.

In FIG. 6, monitoring devices 101a, 101b, 101c each can be the monitoring device 101 described earlier and is connected to a respective client device 102a, 102b, and 102c (e.g., via a respective Bluetooth connection) of a user (e.g., 606a, 606b, 606c). The client devices 102a, 102b, and 102c can each communicate with the server system 622 through one or more data communication networks 613 such as the Internet, for example. As described earlier, a client application 105a (or 105b, 105c) running on the client device 102a (or 102b, 102c) can present a user interface 104a (or 104b, 104c) that is configured to display parameters of a swimming pool the client device floats in and display notifications such as supply level or user actions. For example, the application 105 may facilitate the selection of monitoring parameters such that the monitor collects and send measurements at defined intervals (e.g., daily or hourly) or, in some instances, on a continual basis.

More particularly, a client device (e.g., 102a) can relay measurement data from a connected pool monitoring device (e.g., 101a) to the server system 622, for example, to the device manager 632. The device manager 632 can store the measurement data in the device data database 651. The server system 622 can determine parameters and notifications to be displayed to a user of the client application, and send the data and notifications to the client application running on the client device. The client application then can display the parameters and notifications in its user interface (e.g., 104a). In various implementations, instead of the client device, a bridge device connected the pool monitoring device (e.g., via a Bluetooth connection) can replay measurement data from the monitoring device to the server system 622. In this way, measurement data can be more reliably relayed to the server system 622 in case the client device losses its connection to the pool monitoring device (e.g., when the client device and its user are away from the pool). In some instances, the client device may annotate measurement data with images of the pool, test strips, or other indicators of the state of the pool water. The images may be synchronized with measurement data based, for example, on timestamps electronically associated with the images and the measurement data to increase accuracy of the measurements, for example.

The calculation engine 634 is a software component that is configured to, based on measurement data from a monitoring device (e.g., 101a) in a swimming pool, calculate an amount of a chemical that must be added to the swimming pool. The calculation engine 634 can also estimate the amount of water in the swimming pool. Based on an expected impact (e.g., change in a measured parameter) of the amount of chemical added to a given volume of water, and based on data measured by the monitoring device after the chemical is added to the pool, the calculation engine 634 can measure or predict the actual impact on the pool and/or determine the volume of water in the pool. For instance, if 16 ounces of acid are expected to lower the pH from 7.6 to 7.4 in 10,000 gallons of water, but the pH only drops from 7.6 to 7.5, then calculation engine 634 can estimate that the pool size is around 20,000 gallons. In this way, the calculation engine 634 can continue this volume calculation every time chemicals are added to the pool and refine its estimate of the pool's volume. For instance, if the instruction for the pool is to drop one chemical pod into the pool, but the calculation engine 634 does not see the expected change in chemical readings, the calculation engine 634 can adjust the estimate of the pool size and the next time (e.g., next week) the instruction can include two chemical pods. Again, the calculation engine 634 can examine the impact of those pods, and continue to improve its accuracy over time. Later readings may cause smaller changes to the volume calculation than early readings, thus leading towards a converging estimate, rather than wild fluctuations.

In some instances, the volume calculation may be enhanced or even replaced with volumetric estimates based on photographic data. For example, satellite images of a pool (based on the address of the user, for example) may be used to calculate the surface area of the pool, and when combined with either a calculated depth (based, for example on observed shadows on the pool floor), or an average pool depth (e.g., five feet) result in an accurate estimate of pool volume.

When the calculation engine 634 calculates an amount of a chemical needed for a swimming pool based on measurement data of the pool by a monitoring device (e.g., 101a), the calculation engine 634 can determine a user action corresponding to the calculated amount of the chemical. For instance, a user action can be adding one red pod to the pool. The device manager 632 can send a notification including the user action to the client device (e.g., 102a) of the customer (e.g., 606a). After receiving the notification, the client application 105a can present the user action in its user interface (e.g., 104a).

Instead of sending notifications of user actions whenever a new user action is determined by the calculation engine 634, the server system 622 can combine several user actions in one notification and send the notification to the client device of the customer. The calculation engine 634 can store each determined user action in the actions database 653. The notification engine 636 can collect (scan) user actions (stored in the actions database 653) for a particular customer at a later time (e.g., on a Saturday morning) and send a notification including the collected user actions to the customer, as illustrated in FIG. 7.

When a monitoring device (e.g., 101a) is first shipped to a customer (e.g., 606a), a starting inventory of chemical pods can be included in the initial shipment, for example, 12 red pods, 8 blue pods, 6 green pods, and 4 yellow pods. The starting inventory can be recorded in the inventory data database 652, for example. When the server system 622 sends a notification to the customer for adding a particular number of a particular pod (e.g., 2 red pods) to the pool, the inventory engine 638 subtracts the particular number of the particular pod from the customer's inventory record stored in the inventory data database 652. In addition, when a certain amount of chemicals (e.g., 3 blue pods and 3 green pods) are shipped to the customer, the inventory engine 638 can add the amount of chemicals to the customer's inventory record stored in the inventory data database 652.

The inventory engine 638 can calculate in advance (e.g., one or two months out) chemicals needed by a customer by the customer's inventory record, past usage (historical data), and location. The inventory engine 638 can notify a shipper to ship the chemicals to the customer, or send a notification to the customer for confirmation before shipping the chemicals to the customer.

FIG. 8 illustrates an example algorithm for calculating chemical needs for a pool.

Figure 9:
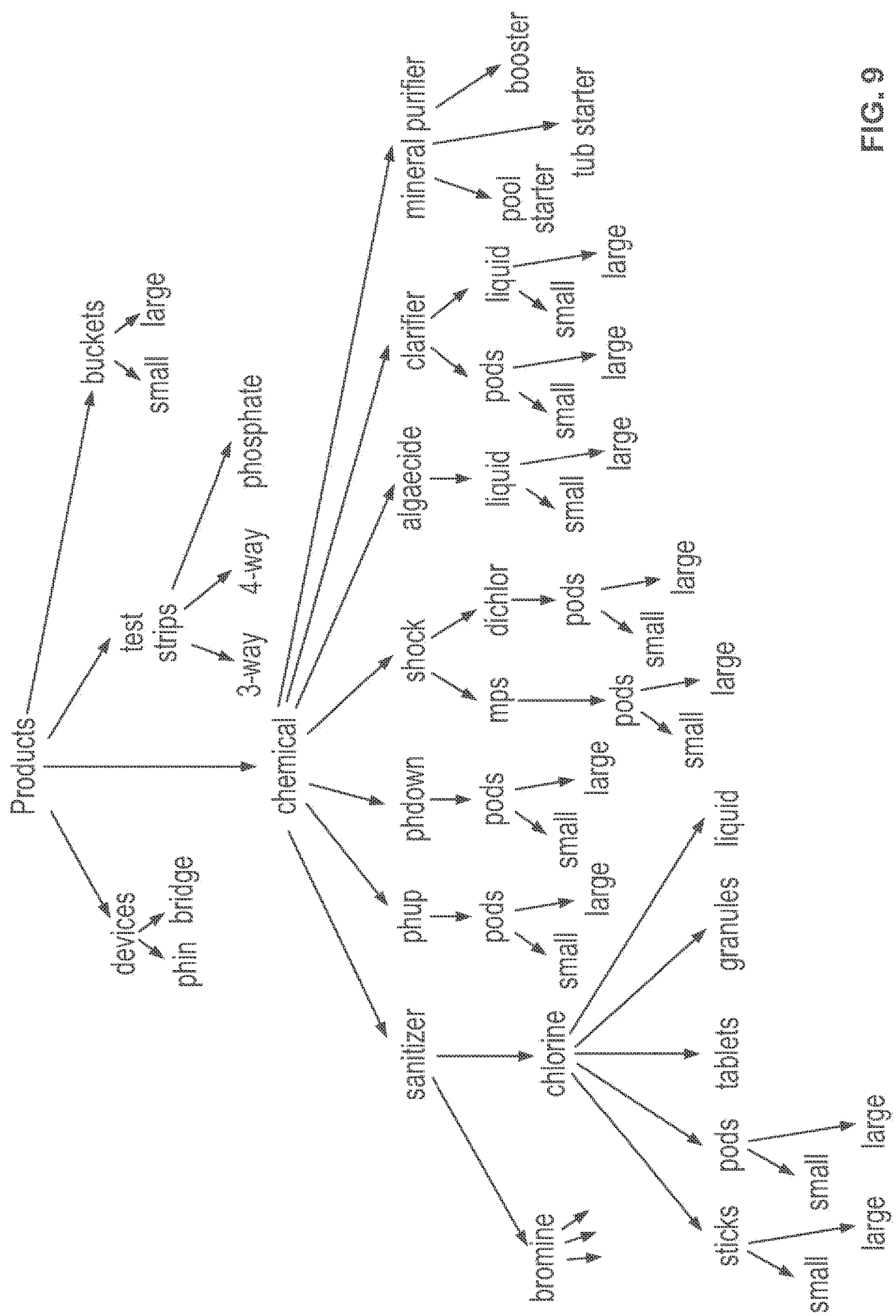
FIG. 9 is an example of a decision tree used to determine appropriate action to take based on measurements obtained by the measurement device in accordance with one embodiment of the invention.

FIG. 9 illustrates an example a decision tree used by the systems and methods to determine appropriate action to take based on measurements obtained by the measurement device 101.

The server system 622 can identify potential problems based on device data stored in the device data database 651. For instance, an automatic water filler can automatically replenish water to a pool to a preset water level if the pool loses water due to evaporation or leakage (e.g., a crack on a side or bottom of the pool). The server system 622 can identify a potential leakage problem of a particular pool using the monitoring device 101 based on measurement data from other monitoring devices used in pools in the vicinity (e.g., within five-mile radius) of the particular pool, for example, if the particular pool has chemicals diluted faster than the neighboring pools (which would see similar level of evaporation).

The server system 622 can be configured to store records of a service network of certified pool technicians. A customer (e.g., user 606c) can send a request from a client application (e.g., 105c) for a particular pool maintenance job. After receiving the request, the server system 622 can select a technician from the records based on the particular job and levels of skills or certifications required, and notify the selected technician. Alternatively or additionally, the technician may be selected based on location of the technician with respect to the pool and/or based on one or more of the following: technician availability, consumer preference, technician preference, availability, rating, etc. Charges for pool maintenance jobs can be negotiated in advance and stored with the records of the service network of technicians. The server system 622 can store customer rating on pool technicians with the record. The server system 622 can remove a particular technician form the service network if the corresponding customer rating is below a threshold, for example.

Figure 10:
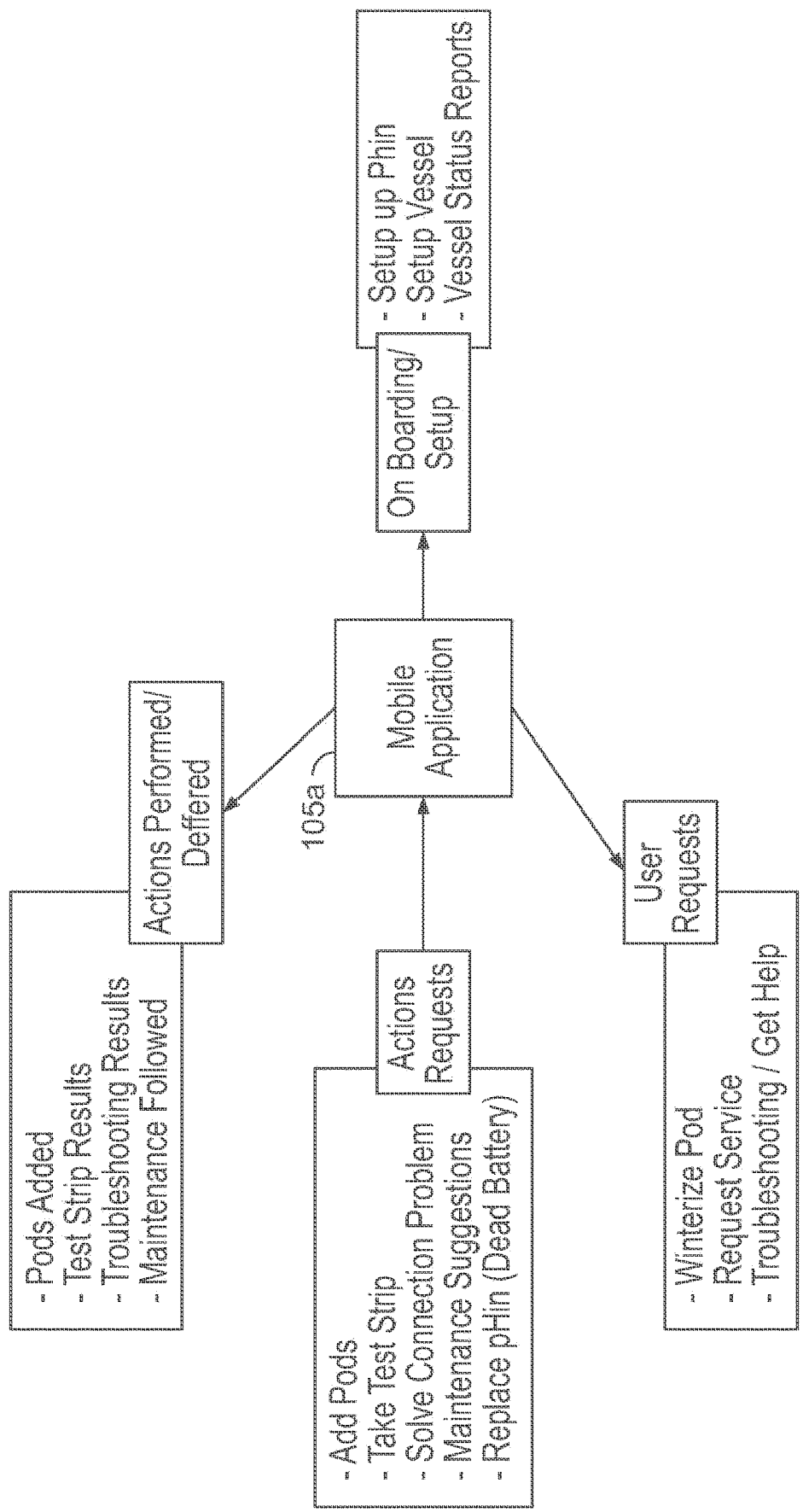
FIG. 10 is a data flow diagram used by a mobile application as part of the system of FIG. 6 in accordance with one embodiment of the application.

FIG. 10 is a data flow diagram of a mobile application such as the client application 105a shown in FIG. 6. As describer earlier, the server system 622 can send user actions (e.g., "add pods") to the client application to be presented in the application's user interface (e.g., 104a). The customer (e.g., 606a) can access the client application and record actions (e.g., "pods added" that are performed. The client application can send the recorded actions to the server system 622, which in turn stores the recorded actions in the device data database 651, inventory data database 652, or actions database 653. In addition, the user can access the client application and send requests (e.g., troubleshooting) to the server system 622. The client application can also present user interfaces for the customer to set up or register (on-boarding) with the server system 622.

Figure 11:
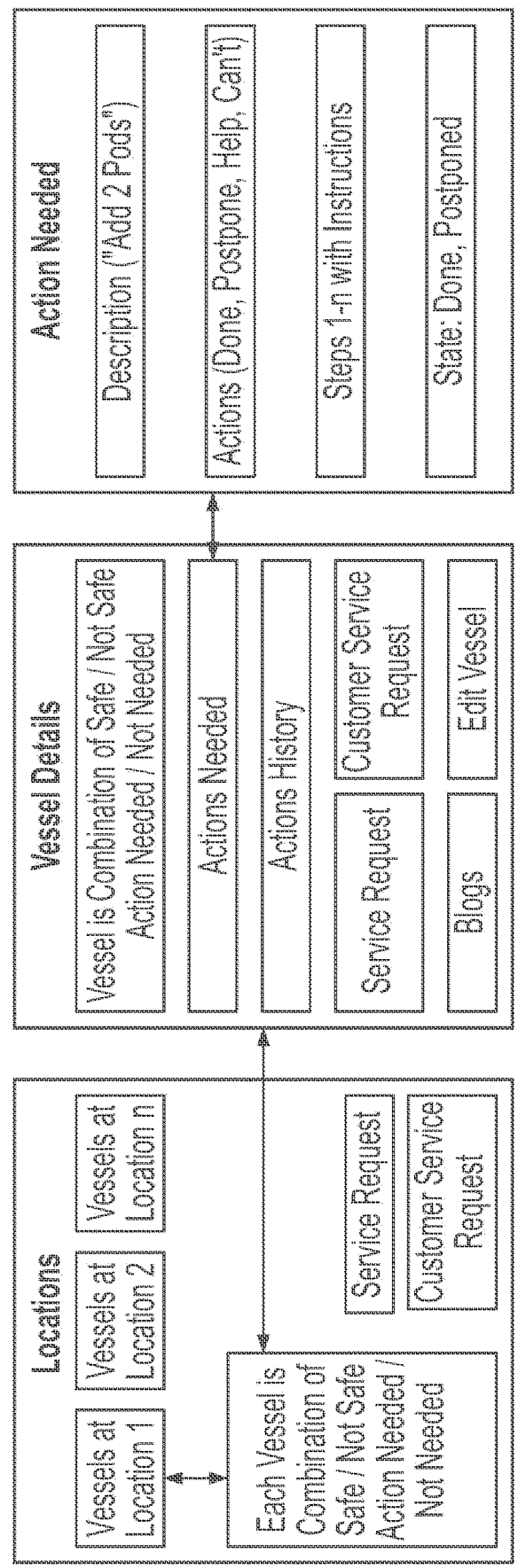
FIG. 11 is an example of a data storage diagram for storing data collected and generated by the system of FIG. 6 and in accordance with one embodiment of the invention.

The server system 622 can store in the device data database 651 and actions data database 653 information and actions associated with each monitoring devices or vessels such as the monitoring devices 101a, 101b, and 101c, as shown in FIG. 11. For each monitoring device, the server system 622 can store a location, action status, service request, user actions to be performed, and user action history, for example. The server system 622 can store other types of information and actions associated with a monitoring device.

The server system 622 and calculation engine can also use the measurement data from the device data database 651 to identify trends for individual pools, neighborhoods or larger demographic areas. For example, data collected over a period of time may indicate that, on average, a particular pool requires certain actions on a regular basis. In such cases, measurements that deviate from the predicted data trend may be ignored, either completely or until corroborating measurements are received. The trend data may be partitioned or segmented to account for seasonal changes (e.g., winter versus summer), usage patterns, etc. such that certain measurements that might have been ignored under some conditions result in actions in others.

The trend data may be used to build protocols that represent a higher-order treatment routines, which in turn may be attributed to certain pools or spas. For example, a protocol may be derived that represents a 25,000-30,000 gallon pool with over 75% sun exposure and moderate use in a certain geographic zone. Pools may be assigned to geographic zones based on latitude/longitude pairs, zip codes, or agricultural zones such as the plant hardiness zone map. The protocol may then be assigned to new pools as they are added to the service such that limited or no data need be collected before scheduling a treatment regimen. Protocols may also be used to identify outlier measurements, or, in some cases, used to initiate actions when the device is inactive.

Figure 12:
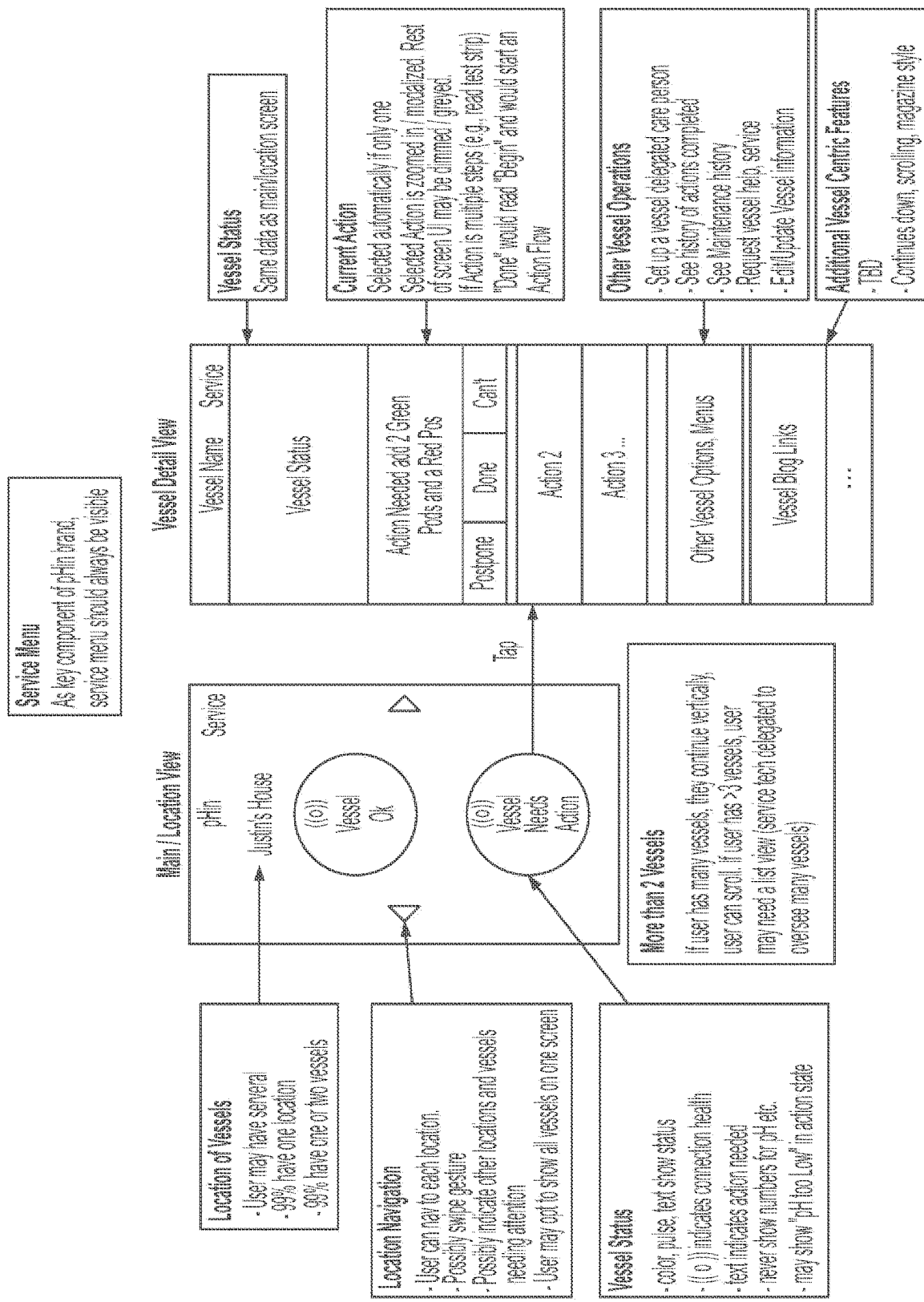
FIG. 12 illustrates exemplary wire frames for a client application used within the system of FIG. 6 and in accordance with one embodiment of the invention.
Figure 14:
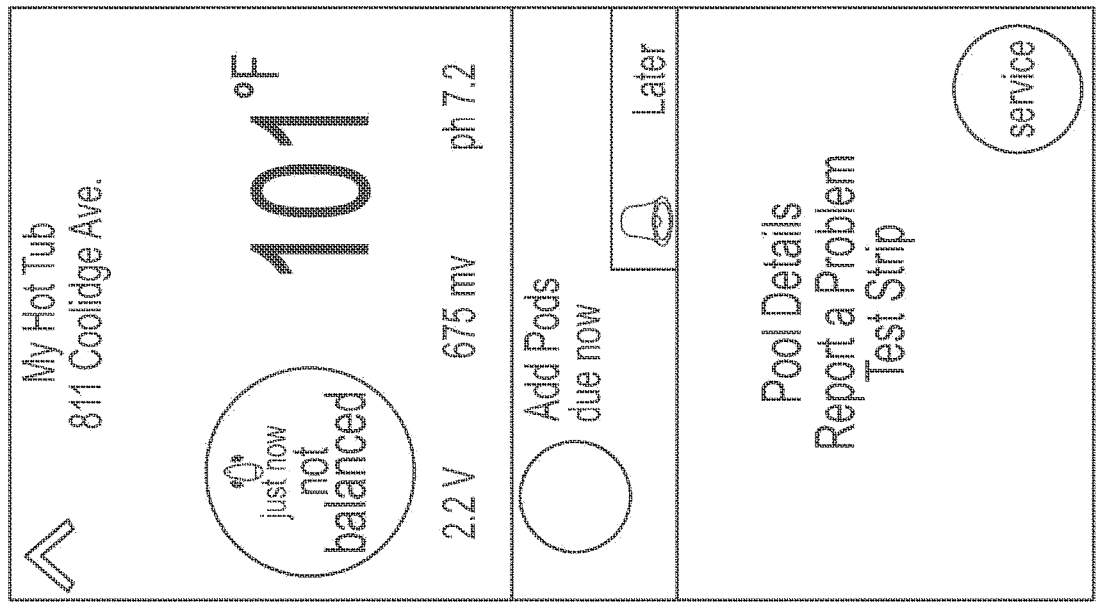
FIG. 14 is an exemplary screen from the client application of FIG. 12 in accordance with one embodiment of the invention.
Figure 13:
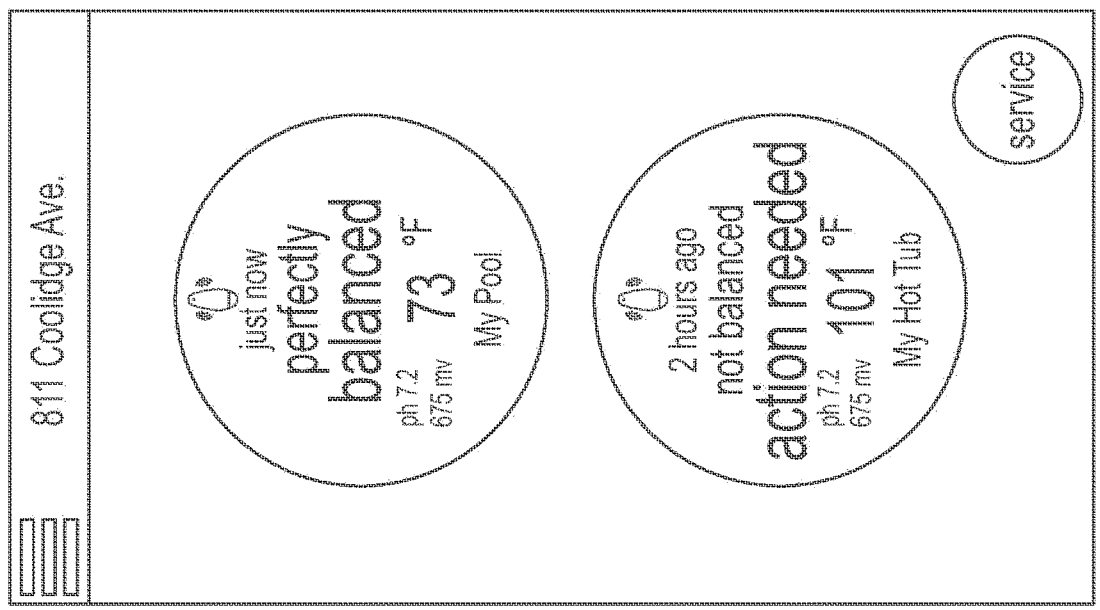
FIG. 13 is an exemplary screen from the client application of FIG. 12 in accordance with one embodiment of the invention.
Figure 15:
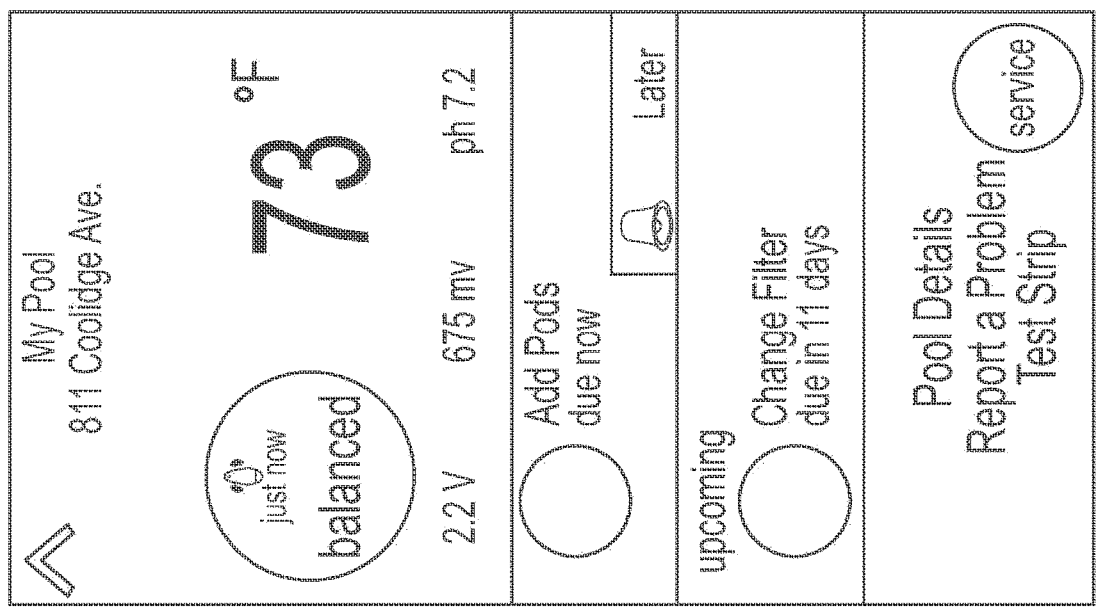
FIG. 15 is an exemplary screen from the client application of FIG. 12 in accordance with one embodiment of the invention.

FIG. 12 illustrates example wire frames of a user interface (e.g., 104a) of a client application (e.g., 105a) running on a client device (e.g., 102a) that communicates with the server system 622. The user interface can include a location (e.g., "Justin's House"), status of a monitoring device 101 (e.g., "Vessel Ok"), and an icon for user actions (e.g., "Vessel Needs Actions"), for example. FIGS. 13-15 illustrate example screens of the user interface.

Figure 16:
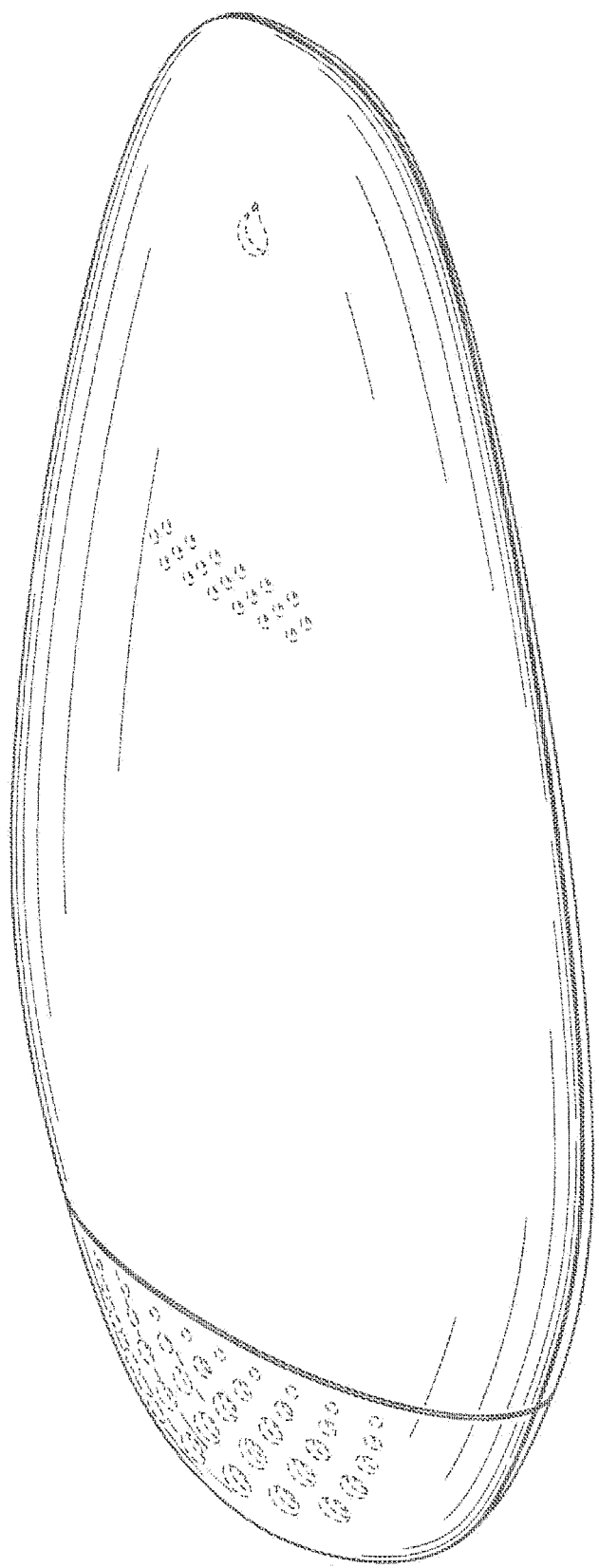
FIGS. 16-23 are further illustrations of a device in accordance with one embodiment of the invention.
Figure 17:
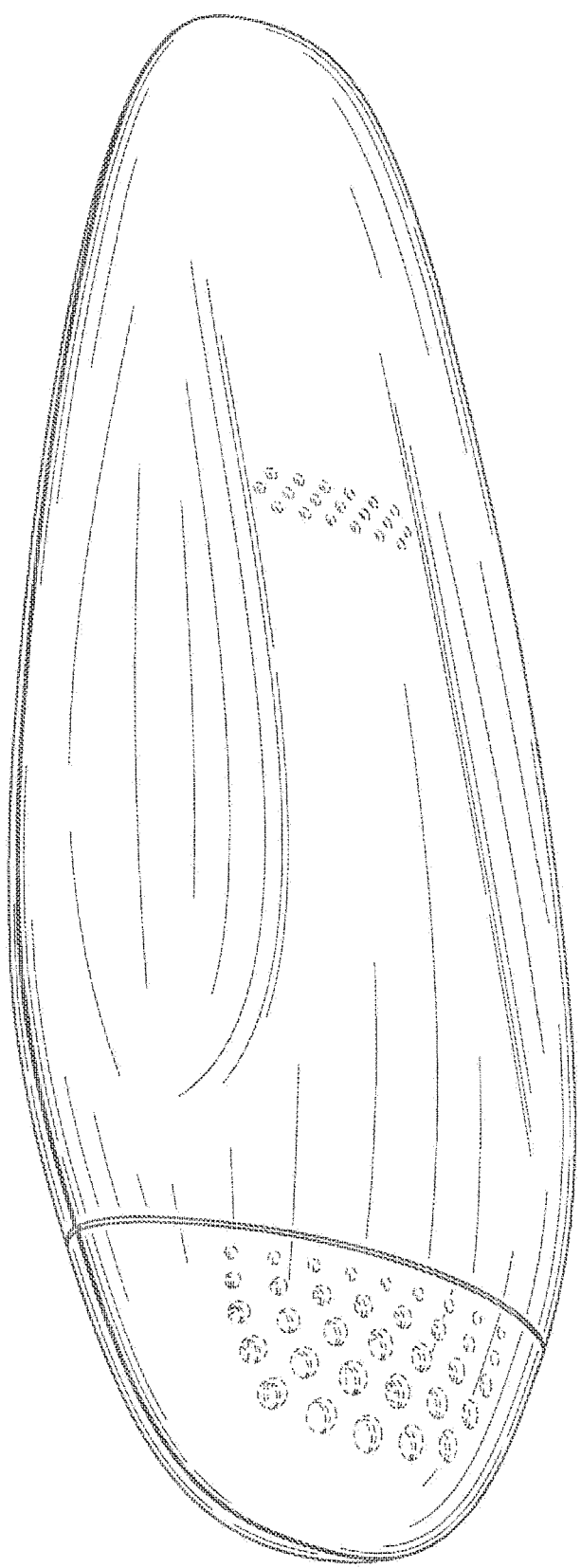
Figure 18:
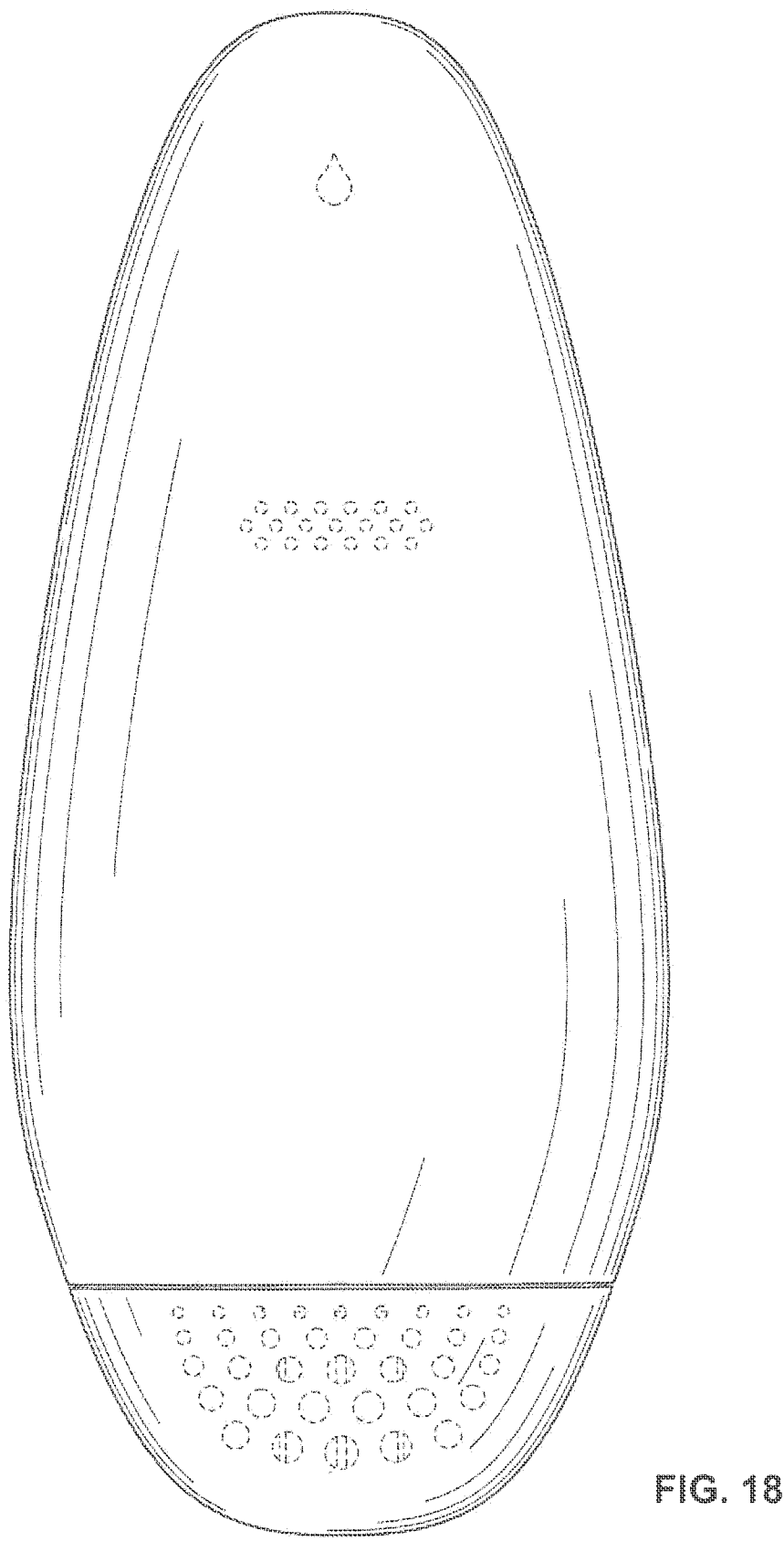
Figure 19:
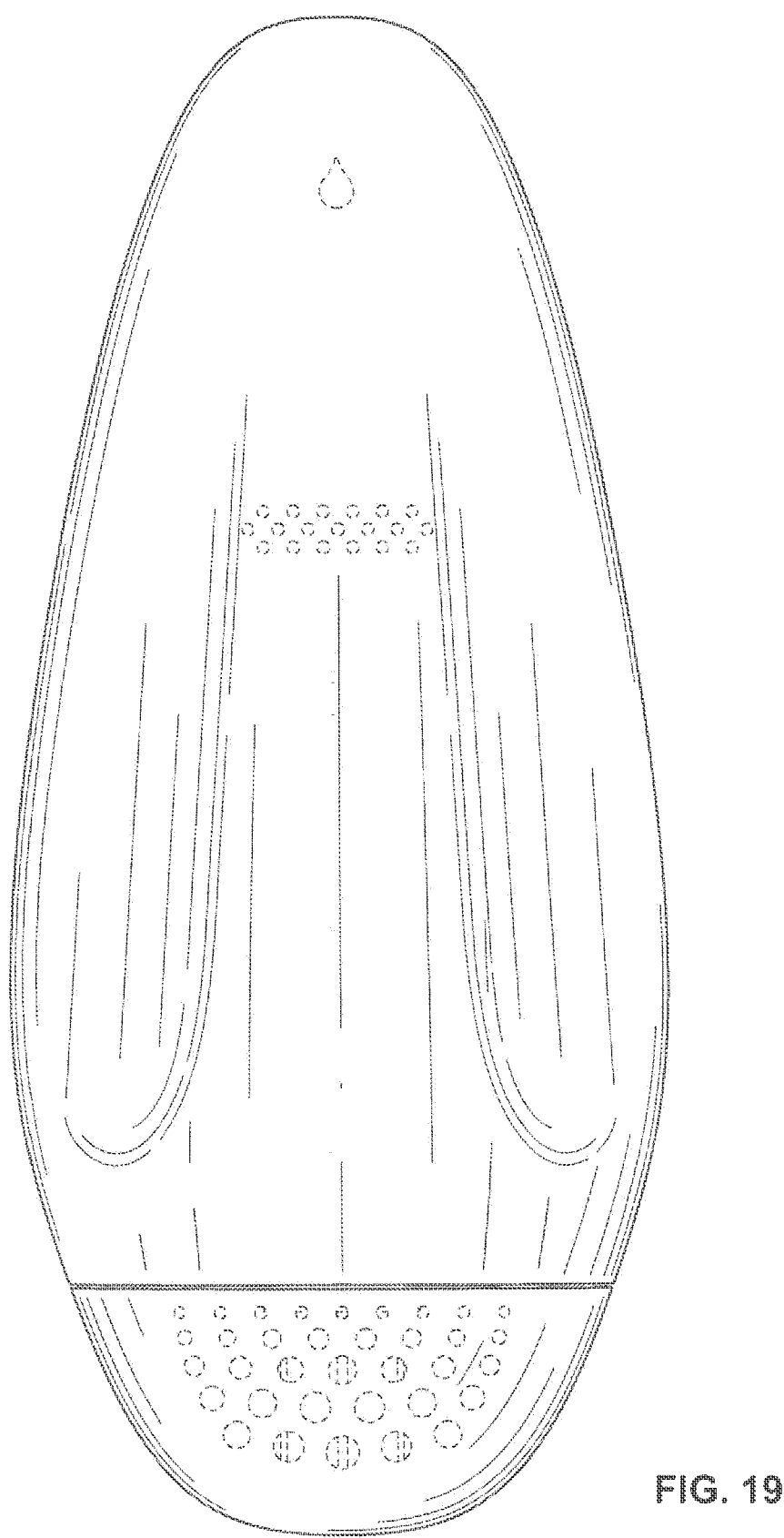
Figure 20:
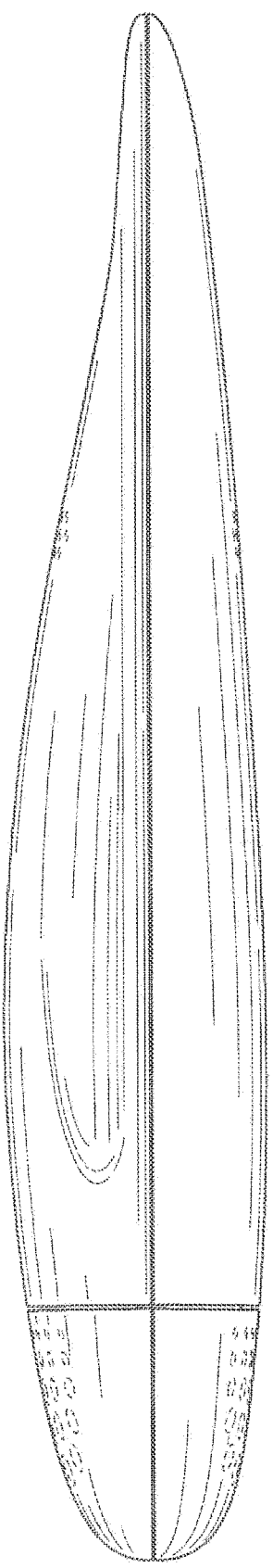
Figure 21:
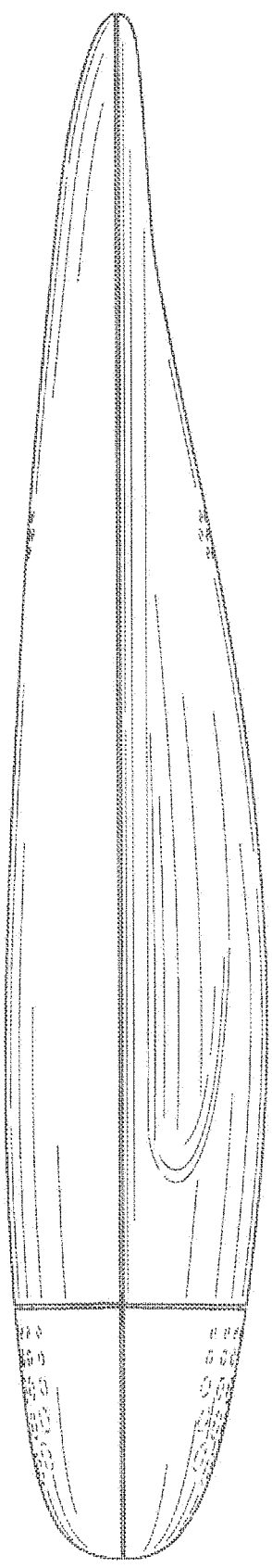
Figure 22:
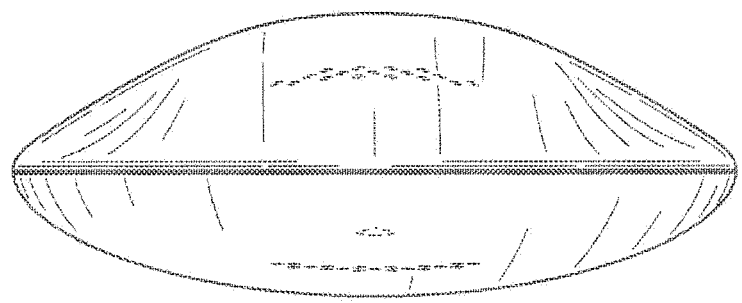
Figure 23:
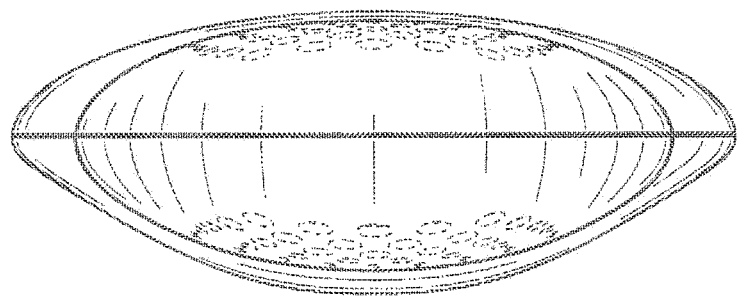

FIGS. 16-23 include additional views of an example monitoring device 101. Specifically, FIG. 16 is a front perspective view, FIG. 17 is a rear perspective view, FIG. 18 is a front view, FIG. 19 is a rear view, FIG. 20 is a left side view, FIG. 21 is a right side view, FIG. 22 is a top view, and FIG. 23 is a bottom view of the monitoring device 101.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language resource), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a smart phone, a smart watch, a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A system for coordinating maintenance on a body of water, comprising:
 a monitoring device configured to monitor one or more parameters associated with a body of water and wirelessly transmit measurement data relating to the one or more parameters associated with the body of water being monitored; and
 a server including a processor and a memory storing records of a service network of certified technicians, the server:
  receiving the measurement data relating to the one or more parameters of the body of water monitored by the monitoring device, determining that a portion of the measurement data was collected while the monitoring device was not in the body of water, processing the measurement data, excluding the portion of the measurement data that was determined to have been collected while the monitoring device was not in the body of water, to identify a problem associated with the body of water monitored by the monitoring device, receiving a request from a customer for the performance of a maintenance job on the body of water, selecting a technician from the service network of certified technicians to perform the maintenance job based on the maintenance job, and notifying the selected technician of the maintenance job.

2. The system of claim 1, wherein the system determines a level of skill required to perform the maintenance job and selects the technician based at least in part on the determined level of skill.

3. The system of claim 1, wherein the system determines a certification required to perform the maintenance job and selects the technician based at least in part on the determined certification.

4. The system of claim 1, wherein the system selects the technician based on at least one of a location of the technician with respect to the body of water, an availability of the technician, a technician preference of the customer, and a rating of the technician.

5. The system of claim 1, wherein the records stored in the memory include a rating for each of the certified technicians.

6. The system of claim 5, wherein the system receives from the customer a rating of the technician selected to perform the maintenance job and updates the rating stored in the memory for the technician based on the rating received from the customer.

7. The system of claim 6, wherein the system removes the technician from the service network of certified technicians if the rating stored in the memory for the technician is below a threshold rating value.

8. The system of claim 1, wherein the system receives a charge for the maintenance job and stores the charge in the records.

9. The system of claim 1, wherein the memory includes a device data database and the server stores the received measurement data in the device data database.

10. The system of claim 1, wherein the monitoring device wirelessly transmits the measurement data to a client device and the client device transmits that measurement data to the server.

11. A system for coordinating maintenance on a body of water, comprising:

a server including a processor and a memory storing records of a service network of certified technicians, the server:

receiving measurement data relating to one or more parameters of a body of water monitored by a monitoring device, determining that a portion of the measurement data was collected while the monitoring device was not in the body of water, processing the measurement data, excluding the portion of the measurement data that was determined to have been collected while the monitoring device was not in the body of water, to identify a problem associated with the body of water monitored by the monitoring device, receiving a request from a customer for the performance of a maintenance job on the body of water, selecting a technician from the service network of certified technicians to perform the maintenance job based on the maintenance job, and notifying the selected technician of the maintenance job.

12. The system of claim 11, wherein the system determines a level of skill required to perform the maintenance job and selects the technician based at least in part on the determined level of skill.

13. The system of claim 11, wherein the system determines a certification required to perform the maintenance job and selects the technician based at least in part on the determined certification.

14. The system of claim 11, wherein the system selects the technician based on at least one of a location of the technician with respect to the body of water, an availability of the technician, a technician preference of the customer, and a rating of the technician.

15. The system of claim 11, wherein the records stored in the memory include a rating for each of the certified technicians.

16. The system of claim 15, wherein the system receives from the customer a rating of the technician selected to perform the maintenance job and updates the rating stored in the memory for the technician based on the rating received from the customer.

17. The system of claim 16, wherein the system removes the technician from the service network of certified technicians if the rating stored in the memory for the technician is below a threshold rating value.

18. The system of claim 11, wherein the system receives a charge for the maintenance job and stores the charge in the records.

19. The system of claim 11, wherein the memory includes a device data database and the server stores the received measurement data in the device data database.

20. The system of claim 11, wherein the server receives the measurement data from the monitoring device or from a client device.

21. A method of coordinating maintenance on a body of water, comprising:

providing a swimming pool monitoring system having a server and a monitoring device configured for wireless communication;

receiving, at the server, measurement data relating to one or more parameters of a body of water monitored by the monitoring device, the server including a processor and a memory storing records of a service network of certified technicians;

processing, at the server, the measurement data to identify a problem associated with the body of water monitored by the monitoring device;

receiving, at the server, a request from a customer for the performance of a maintenance job on the body of water;

selecting a technician from the service network of certified technicians to perform the maintenance job based on the maintenance job; and notifying the selected technician of the maintenance job.

22. The method of claim 21, comprising:

determining a level of skill required to perform the maintenance job, wherein the step of selecting the technician is based at least in part on the determined level of skill.

23. The method of claim 21, comprising:
  determining a certification required to perform the maintenance job,
  wherein the step of selecting the technician is based at least in part on the determined certification.

24. The method of claim 21, wherein the step of selecting the technician is based on at least one of a location of the technician with respect to the body of water, an availability of the technician, a technician preference of the customer, and a rating of the technician.

25. The method of claim 21, wherein the records stored in the memory include a rating for each of the certified technicians.

26. The method of claim 25, comprising:
  receiving from the customer a rating of the technician selected to perform the maintenance job; and
  updating the rating stored in the memory for the technician based on the rating received from the customer.

27. The method of claim 26, comprising:
  removing the technician from the service network of certified technicians if the rating stored in the memory for the technician is below a threshold rating value.

28. The method of claim 21, comprising:
  receiving a charge for the maintenance job; and
  storing the charge in the records.

29. The method of claim 21, comprising:
  storing the received measurement data in a device data database of the memory.

30. The method of claim 21, wherein the server receives the measurement data from the monitoring device or from a client device.

31. The system of claim 1, wherein the maintenance job is based at least in part on the identified problem.

32. The system of claim 11, wherein the maintenance job is based at least in part on the identified problem.

33. The method of claim 21, wherein the maintenance job is based at least in part on the identified problem.

34. The system of claim 1, wherein the server identifies a trend based on the measurement data, identifies a portion of the measurement data that deviates from the trend, and excludes the portion of the measurement data that deviates from the trend from the measurement data that is processed to identify a problem associated with the body of water monitored by the monitoring device.

35. The system of claim 11, wherein the server identifies a trend based on the measurement data, identifies a portion of the measurement data that deviates from the trend, and excludes the portion of the measurement data that deviates from the trend from the measurement data that is processed to identify a problem associated with the body of water monitored by the monitoring device.

36. The method of claim 21, comprising:
  identifying a trend based on the measurement data; and
  identifying a portion of the measurement data that deviates from the trend,
  wherein the portion of the measurement data that deviates from the trend is excluded from the measurement data that is processed to identify a problem associated with the body of water monitored by the monitoring device.

37. The system of claim 1, wherein the monitoring device comprises:
  a container configured to be partially submerged in a body of water;
  a sensor disposed within a submerged portion of the container, the sensor configured to measure at least one of the one or more parameter associated with the water; and
  an electronic component disposed within an unsubmerged portion of the container, the electronic component configured to wirelessly transmit the measurement data relating to the one or more parameters associated with the body of water being monitored.

38. The system of claim 11, comprising the monitoring device,
  wherein the monitoring device comprises:
    a container configured to be partially submerged in a body of water;
    a sensor disposed within a submerged portion of the container, the sensor configured to measure at least one of the one or more parameter associated with the water; and
    an electronic component disposed within an unsubmerged portion of the container, the electronic component configured to wirelessly transmit the measurement data relating to the one or more parameters associated with the body of water being monitored.

39. The method of claim 21, wherein the monitoring device comprises:
  a container configured to be partially submerged in a body of water;
  a sensor disposed within a submerged portion of the container, the sensor configured to measure at least one of the one or more parameter associated with the water; and
  an electronic component disposed within an unsubmerged portion of the container, the electronic component configured to wirelessly transmit the measurement data relating to the one or more parameters associated with the body of water being monitored.

* * * * *